United States Patent [19]
Sheppard et al.

[11] Patent Number: 5,399,968
[45] Date of Patent: Mar. 21, 1995

[54] EDDY CURRENT PROBE HAVING BODY OF HIGH PERMEABILITY SUPPORTING DRIVE COIL AND PLURAL SENSORS

[75] Inventors: William R. Sheppard, Granada Hills; Kent K. Tam, Monterey Park, both of Calif.

[73] Assignee: Northrop Grumman Corporation, Los Angeles, Calif.

[21] Appl. No.: 126,944

[22] Filed: Sep. 24, 1993

Related U.S. Application Data

[63] Continuation of Ser. No. 830,042, Jan. 31, 1992, abandoned.

[51] Int. Cl.⁶ .......................................... G01N 27/90
[52] U.S. Cl. ...................... 324/242; 324/232; 324/235; 324/262
[58] Field of Search ............... 324/226, 227, 232, 233, 324/235, 237–243, 262

[56] References Cited

U.S. PATENT DOCUMENTS

| | | | |
|---|---|---|---|
| 2,965,840 | 12/1960 | Renken, Jr. et al. | 324/240 X |
| 3,109,139 | 10/1963 | Branker | 324/240 |
| 3,437,918 | 4/1969 | Arnelo | 324/238 |
| 3,449,664 | 6/1969 | Smith | 324/235 |
| 3,497,799 | 2/1970 | Harmon | 324/237 |
| 3,694,740 | 9/1972 | Bergstrand | 324/238 |
| 4,095,181 | 6/1978 | Harris et al. | 324/238 |
| 4,219,774 | 8/1980 | Rogel et al. | 324/238 |
| 4,271,393 | 6/1981 | Hansen et al. | 324/240 |
| 4,414,508 | 11/1983 | Davis et al. | 324/238 |
| 4,445,089 | 4/1984 | Harrison | 324/238 |
| 4,495,466 | 1/1985 | Lakin | 324/242 |
| 4,496,904 | 1/1985 | Harrison | 324/238 |
| 4,534,405 | 8/1985 | Hulek et al. | 324/238 |
| 4,677,379 | 6/1987 | Arnaud et al. | 324/242 |
| 4,734,642 | 3/1988 | Törnblom | 324/238 |
| 4,855,677 | 8/1989 | Clark, Jr. et al. | 324/238 |
| 5,021,738 | 6/1991 | Vernon et al. | 324/242 X |

FOREIGN PATENT DOCUMENTS

| | | | |
|---|---|---|---|
| 162448 | 9/1984 | Japan | 324/242 |
| 147648 | 8/1985 | Japan | 324/242 |
| 14569 | 1/1986 | Japan | 324/242 |
| 631987 | 11/1949 | United Kingdom | 324/242 |
| 1155930 | 5/1985 | U.S.S.R. | 324/242 |

OTHER PUBLICATIONS

"Eddy Current Imaging System," Bruce F. Fields, NBS Staff Report PB80-976300, Feb. 1980.
U.S. Department of Commerce, National Bureau of Standards, Washington, D.C. 20234.

Primary Examiner—Gerard R. Strecker
Attorney, Agent, or Firm—Terry J. Anderson; Karl J. Hoch, Jr.

[57] ABSTRACT

An eddy current probe for detection of cracks in multilayered structures. The probe includes a body of a material having high permeability and is shaped to include a central core and an additional wall. A central core drive coil is wound around the central core of the body and a plurality of sense coils are located in an array in association with the additional wall. An outer drive coil is wound about the outside of the additional wall. The central core drive coil is excited with a first alternating current high frequency signal producing eddy currents primarily in the top of the layered structure. These eddy currents are sensed with the sense coil array and analyzed for structural defects in the top surface of the layered structure. The central core coil is excited with a second alternating current signal of a lower frequency than the first signal producing eddy currents in deeper layers of the structure. Such eddy currents are sensed by the sense coils and the signals so sensed are stored. The outer drive coil is excited with a low frequency signal and the sense coils operated to detect eddy currents in deeper layers of the structure. The signal from excitation of the outer drive coil is scaled with respect to the signal from the central core drive coil for separating signal indicative of defects from that indicative of differences in the structure of the underlying components of the layered structure. The probe may be circular or linear.

42 Claims, 11 Drawing Sheets

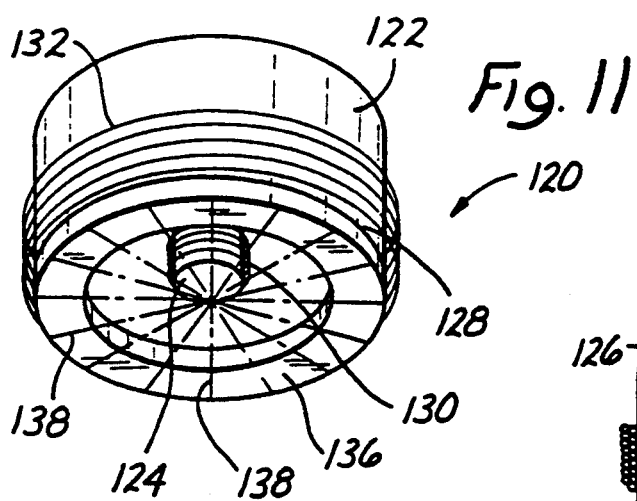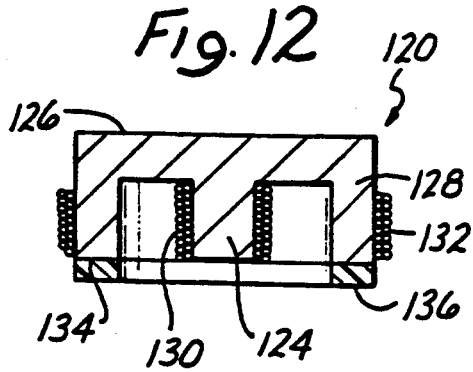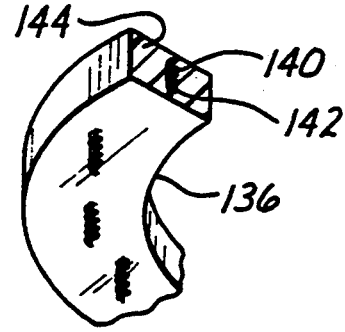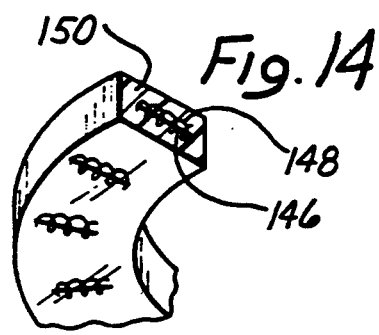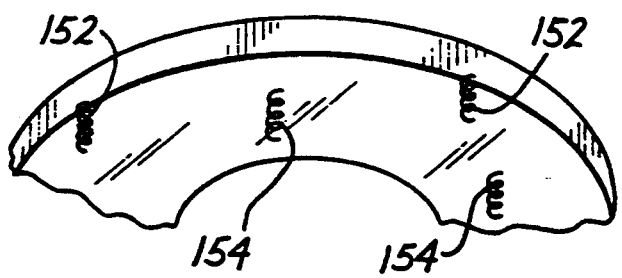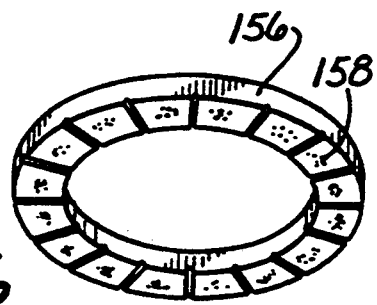

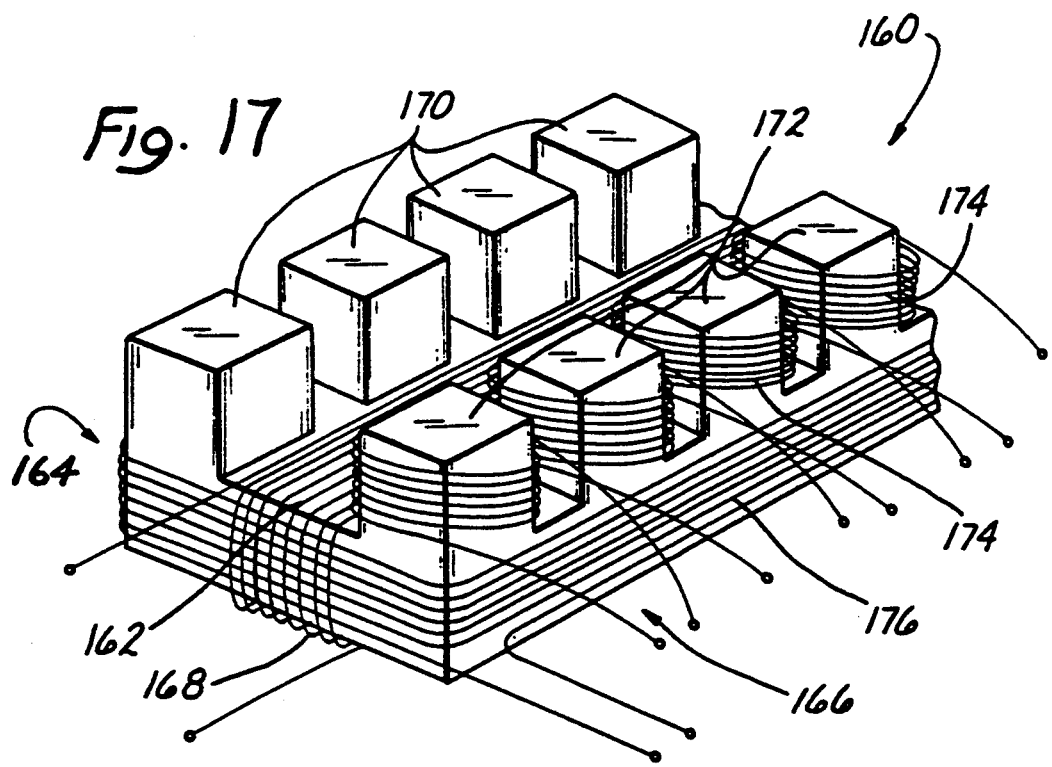
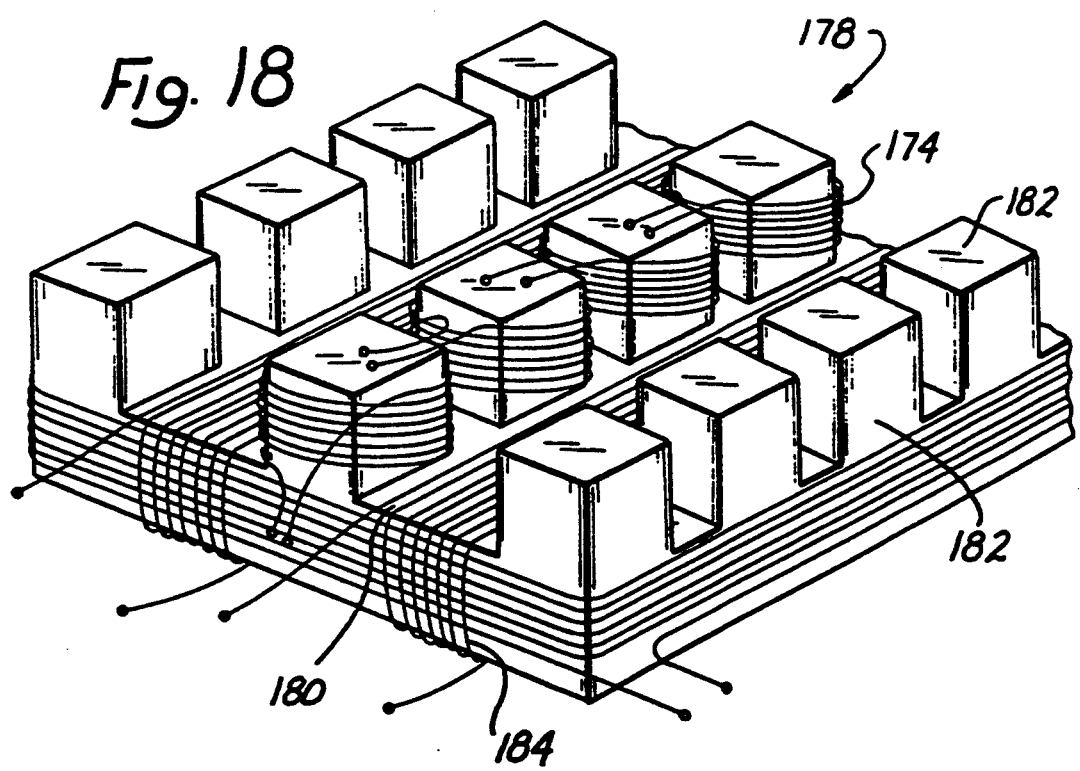

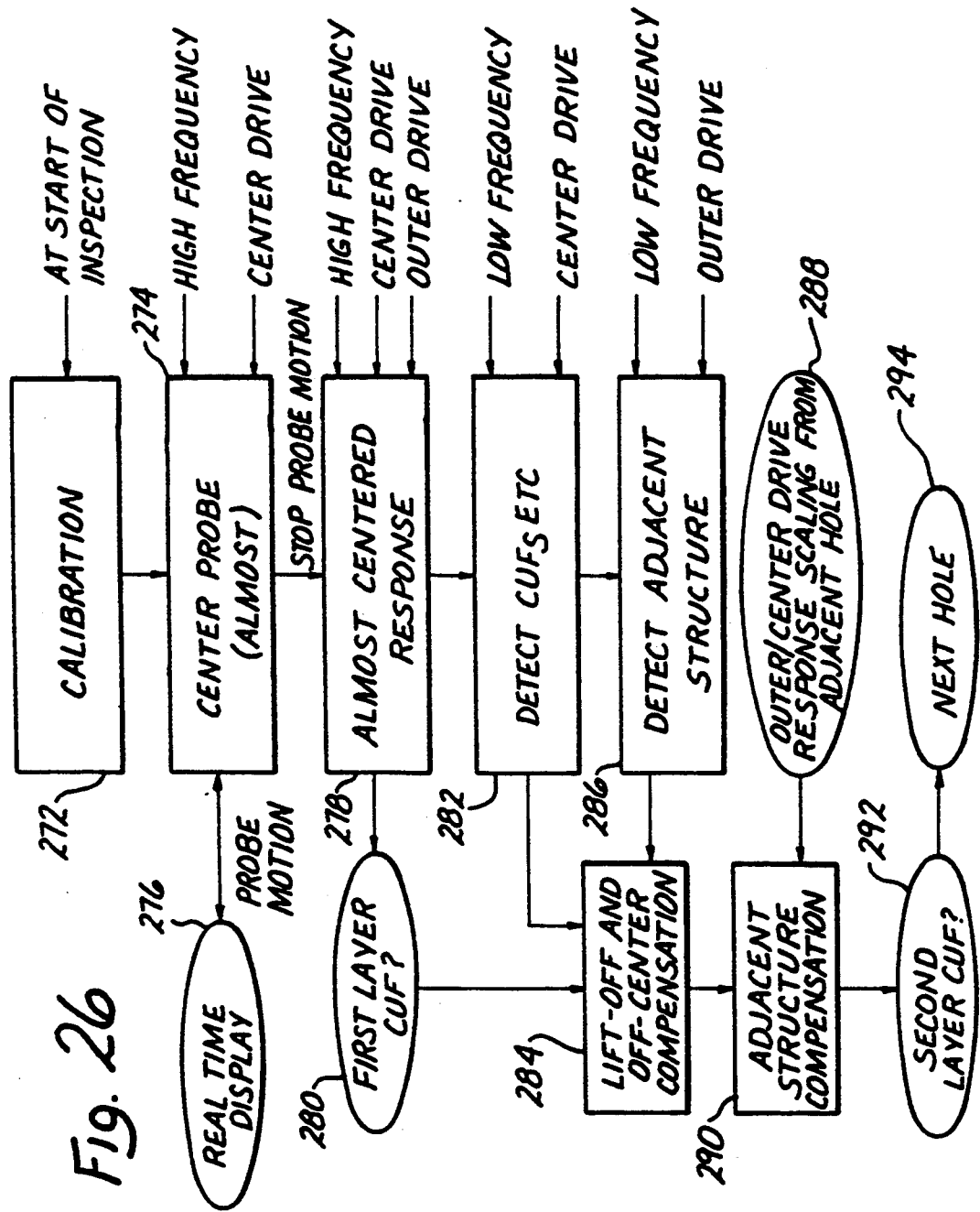

EDDY CURRENT PROBE HAVING BODY OF HIGH PERMEABILITY SUPPORTING DRIVE COIL AND PLURAL SENSORS

CROSS-REFERENCE TO RELATED APPLICATIONS

This application is a continuation application of commonly-assigned application Ser. No. 07/830,042, filed Jan. 31, 1992, now abandoned.

BACKGROUND OF THE INVENTION

1. Field of the Invention

This invention is directed to devices for detecting cracks, flaws and other defects in a layered structure. More specifically, the devices utilize eddy currents that are generated within the layers of the structure for the detection of the cracks, flaws and other defects in the layers of the structure.

2. Description of Related Art

Various instruments for flaw detection in structures have been developed that rely upon the generation of eddy currents in the body of the structure being tested. Flaws in the metallic structures are detected by their perturbation of the eddy currents. The eddy currents are generated in the metallic structures by positioning the structures within an alternating magnetic field. Perturbation of the eddy currents because of the localized presence of a defect in the metallic structure creates a resultant change in the magnetic flux associated with these eddy currents. When such change is detected, it is an indication of the presence of defects in the structure. Such use of eddy currents has been practiced for detecting flaws in solid metallic slabs, metallic pipes, and in layered metallic structures such as the outside surfaces of aircraft.

U.S. Pat. No. 3,437,918 to Arnelo describes an eddy current detection system for a slab structure. Further, eddy current detection systems for slabs are described in U.S. Pat. No. 4,534,405 to Hulek, et al., U.S.S.R. patent 1,155,930, Japanese patent 60-147648, and Japanese patent 59-162448. Eddy current detection for solid pipe like structures is disclosed in U.S. Pat. No. 3,694,740 to Bergstrand, et al., Japanese patent 61-14569, British patent 631,987 to Rudorff, and U.S. Pat. No. 4,855,677 to Clark, et al. Detection systems for layered structures are found in U.S. Pat. Nos. 4,219,774 to Rogel, et al., 4,414,508 to Davis, et al., 4,495,466 to Lakin, et al., 4,496,904 to Harrison, 4,445,089 to Harrison, 4,677,379 to Arnaud, et al., and 4,095,181 to Harris et al.

Many of the above patents describe systems wherein a single coil is utilized to induce a magnetic field in a test piece. Flaws are detected by noting changes in the impedance of the test coil. In other of the above patents, both a drive coil and a sense coil are utilized. Generally, detection of flaws is achieved utilizing voltage variations in the sense coil. The voltage variations are detected utilizing a null bridge.

In the above noted Clark patent, U.S. Pat. No. 4,855,677, a plurality of coaxial coils, each driven at a different frequency, is utilized to detect flaws at different depths in pipes. In the above noted Japanese patent 59-162448, the sense elements, which are independent of the drive coil, are arranged in two sets along two radii which are 180° apart. The sets of sense coils are rotated directly underneath the center of the drive coil.

As is described in the noted Lakin patent, U.S. Pat. No. 4,495,466, the skins on wings and the body of aircraft are constructed by fastening several layers together with a large number of fasteners. Each of the fasteners is positioned in a hole that passes through each of the layers. Fatigue cracks about the fastener holes develop in response to stress of the aircraft structures.

In aircraft structures, if these cracks are detected when they are small, the fastener having the crack adjacent thereto can be removed, the hole drilled out to a slightly larger diameter that includes the crack within its bounds, and a larger fastener inserted. This thus removes the crack and, in doing so, eliminates a structural defect without severely compromising the integrity of the part that initially bore the defect.

For aircraft structures or other structures, the above noted U.S. Pat. No. 4,219,774 to Rogel and U.S. Pat. No. 4,414,508 to Davis require removal of the fastener for inspection of the fastener holes. This is a time consuming and laborious process. Further, aside from the time and expense, in the process of removing the fasteners new flaws can be introduced into the layered structure.

In order to sense defects in deeper layers, as for instance a second layer of a two layer system, expedients have been devised for separating signal from the first layer from that of the second layer. Such expedients include multiple frequency sensing as discussed in the above noted U.S. Pat. No. 4,495,466 to Lakin, or sensor movement as is common in above noted U.S. Pat. Nos. 4,095,181 to Harris, 4,445,089 and 4,496,904 to Harrison, and 4,677,379 to Arnaud. While the methods practiced in these patents have resulted in improvements over older methods, flaw detection is still a difficult and time consuming process.

Composite materials have been increasingly used in aircraft construction, especially military aircraft. Such composite materials serve to shield detection of flaws in the deeper, underlying metallic structures on which the composite materials are fastened. Additionally, the underlying metallic structures tend to be of complex shape that can distort detection systems such as that of the above noted Arnaud U.S. Pat. No. 4,677,379. This arises because the Arnaud patent relies upon uniform probe movement along uniformly spaced rivet arrays in essentially flat uniform structures. Indeed, as is noted in that patent, the sense coils are stated to be separated from the primary windings at a distance that is equal to one-half of the distance separating consecutive rivets in a succession of rivets. This requires that the pattern of the fasteners be very uniform. Such a uniform pattern may or may not be used in those constructions wherein composite materials are fastened to underlying metallic structures.

Quadrature detection is mentioned in both the above noted U.S. Pat. Nos. 4,677,379 to Arnaud, et al. and 4,496,904 to Harrison. Such a detection technique utilizes both a magnitude and a phase component of a signal for analysis of that signal. As noted above, however, the Arnaud patent requires the probe geometry to be related to the fastener geometry, and the Harrison U.S. Pat. No. 4,496,904 patent requires the probe to be rotated directly over the center of the fastener for defect sensing.

And, in an NBS Staff Report for February of 1980, a publication of the National Bureau of Standards of the U.S. Department of Commerce, an eddy current imaging system is described which is said to provide information about the type and shape of surface flaws as well as limited data on sub-surface flaws, but which provides no capability to account for sub-surface structural geometries. Additionally, orthogonal pairs of drive coils on opposing faces of a square array are operated simultaneously with signals 180° out of phase with each other.

Other techniques that have been utilized for the inspection of aircraft structures include radiographic methods. Such radiographic methods, however, miss up to 75% of the cracks because there is a lack of density differences between a part having a small crack and a part not having a crack therein. Further, such detection methods are difficult to implement in many areas of aircraft because the geometry of the aircraft structure prevents placing an x-ray film on one side of the structure and a suitable device for generating x-rays on the other.

SUMMARY OF THE INVENTION

It is an object of this invention to provide improved detection systems for detecting defects in layered structures as, for instance, aircraft structures.

It is a further object of this invention to provide for detection systems that utilize eddy currents that are generated in a metallic layer of a layered structure.

It is a further object of this invention to provide for inspection systems and methods of inspection that can be done in a forthright manner on a complex structure as, for instance, an aircraft, at a reasonable inspection rate as, for instance, less than 30 seconds per fastener inspected, and in a manner that does not require removal of fasteners from the structure being inspected.

It is an additional object of this invention to provide for apparatus and methods of inspecting layered structures wherein a metallic layer is situated underneath a composite layer and where the metallic layer may have a complex shape that differs from one area under inspection to the next area under inspection.

In accordance with these and other objects as will become evident on reading of the remainder of this specification, there is provided an eddy current probe having a body formed of a high permeability material. The body is shaped to include a central core, a radially extending wall radiating from the central core, and a circumferentially extending wall extending from the radially extending wall concentric with the central core. The central core has a central core drive coil wound thereon. The circumferentially extending wall includes a rim that is distal from the radially extending wall. The rim includes a plurality of interstices that divide the rim into a plurality of symmetrical, independent partitions that are symmetrically located about the circumferentially extending wall. The partitions are shaped so as to extend axially and essentially parallel with the axis of the central core, with each of the partitions being shaped to include a portion thereof that is positioned in space in a plane that is essentially perpendicular to the axis of the central core. A plurality of independent sense coils, equal in number to the number of the partitions, are located on the partitions such that a respective one of the sense coils is wound around a respective one of the partitions and each partition includes an independent sense coil wound around that portion of a respective partition that is positioned in the plane in space that is essentially perpendicular to the axis of the central core. As so positioned, each independent partition includes an independent sense coil wound around it. Further, an outer drive coil is wound about the outside of the circumferentially extending wall. In a preferred embodiment, the plurality of interstices and plurality of partitions together form a castellated structure composed of essentially prismatic partitions separated by essentially straight sided crenelated openings.

Further in accordance with this invention, there is provided an eddy current probe that includes a first body formed of a high permeability material and shaped so as to include a central core, a radially extending wall radiating from the central core, and a circumferentially extending wall extending from the radially extending wall concentrically with the central core. The central core includes a central core drive coil wound thereon. The circumferentially extending wall includes a lip distal from the radially extending wall. The probe includes a further body structurally independent of the first body and which is symmetrically divided into a plurality of individual sections. The further body is mounted on the circumferentially extending wall of the first body in association with the lip of that wall. A plurality of independent transducer means equal in number to the number of the individual sections of the further body are located on the further body such that a respective one of the transducer means is positioned in respect to a respective one of the individual sections of the further body, with each of the individual sections including an independent transducer means operatively associated with it. The transducer means are for sensing eddy currents and are located in at least one symmetrical array with respect to the rim of the circumferentially extending wall.

In one preferred embodiment of the invention, the transducer means each comprises a sense coil and at least portions of the further body are formed of a high permeability material. Preferably, such portions of the further body are formed as ferrite cores that are mounted in the further body with a respective sense coil wound around each of the respective ferrite cores. In a first configuration, the sense coils are orientated on the further body such that, when the further body is mounted on the first body, the axis of each of the sense coils is located essentially parallel with the axis of the central core of the first body. In a second configuration, the sense coils are orientated on the further body such that, when the further body is mounted on the first body, the axis of each of the sense coils is positioned in space in a plane that is essentially perpendicular to the axis of the central core of the first body.

In a further preferred embodiment, an outer drive coil is wound around the outside of the circumferentially extending wall. In even further preferred embodiments, the plurality of sense coils is divided into first and second circular arrays with the first circular array positioned radially from the central core at a first radial distance and the second circular array positioned radially from the central core at a second radial distance. The first and second radial distances are different.

In further embodiments of the invention, the central core of the first body is hollow and includes a centering coil that is positioned in the hollow central core. Further, an inner body which is independent of first body and has a central boss thereon is positioned in the hollow central core with the centering coil wound around the inner body central boss.

In even further preferred embodiments of the invention, each of the transducer means referred to above comprises a Hall effect sensor element, with such Hall effect sensor elements positioned in the respective sections on the further body such that together the plurality of Hall effect sensor elements are oriented in at least one symmetrical array with respect to the lip of the circumferentially extending wall. In an even more preferred embodiment, the further body is a monolithic body having said Hall effect sensor elements integrally formed therein.

In even further preferred embodiments of the invention, means are included for moving the first body in a prescribed closed path with respect to the further body. In one embodiment of the invention, the first body rotates about an axis that is parallel to but radially displaced from the axis of the central core of the first body. In a further embodiment, the body oscillates about an axis that is parallel to but is radially displaced from the axis of the central core of the body. However, the first body does not rotate about this axis.

Further in accordance with this invention, there is provided an eddy current probe that includes a linear body formed of a high permeability material. The linear body comprises a first solid elongated section, a first plurality of individual partitions, and a second plurality of individual partitions. The first solid elongated section has opposing sides that extend along the elongated dimension of the first solid elongated section. The first plurality of individual partitions are located in a first linear array along a first of the sides of the first solid elongated section. The second plurality of individual partitions are located in a second linear array along the second of the sides of the first solid elongated section.

As so located, the individual partitions of the first linear array are each spaced apart from one another, are each oriented essentially perpendicular to the first solid elongated section, and are essentially mutually parallel to each other. Further, the individual partitions of the second linear array are also spaced apart from one another, are each orientated essentially perpendicular to the first solid elongated section, and are essentially mutually parallel to each other. A first drive coil is wound around the first solid elongated section between the first and second sides of the first solid elongated section. A plurality of individual sense coils, equal in number to the number of partitions of the second plurality of individual partitions, are located on the second plurality of individual partitions, with a respective one of the individual sense coils wound around a respective one of the partitions of the second plurality of individual partitions such that each partition of the second plurality of individual partitions includes an independent sense coil wound around it. An outer drive coil is wound around the periphery of the linear body of the probe encompassing the sides of the first solid elongated section and exterior to the first drive coil.

In a further embodiment of this linear probe, the linear body includes a second solid elongated section and a third plurality of individual partitions. The second solid elongated section is joined with the first solid elongated section such that the second linear array of the second plurality of individual partitions is located at the joined sides of the first and second solid elongated sections. A second drive coil is wound around the second solid elongated section between the sides of the second section, and the third plurality of partitions are located in a third linear array along the side of the second solid elongated section opposite to the first solid elongated section. The outer drive coil is wound around the joined first and second solid elongated sections, encompassing the respective sides of those sections opposite from their joined sides and exterior to the first and second drive coils.

Further in accordance with this invention, there is provided a method of inspecting a layered structure that includes selecting a probe having a body formed of a high permeability material with the body shaped to include a central core having a central core drive coil wound thereon. The body further includes an additional wall displaced from the central core. The additional wall includes a plurality of sense coils located in association with it and a further drive coil wound on the additional wall. The probe is positioned against the layered structure approximately centered over the area to be inspected. The central core drive coil is driven with a first input signal of a first alternating frequency to generate eddy currents in said structure. The sense coils are operated to detect initial output signals related to eddy currents generated in the structure. The detected initial output signals are analyzed for anomalies indicative of defects in a top layer of the structure. The central core drive coil is driven with a second input signal of a second alternating frequency to generate eddy currents in the structure. The second alternating frequency is selected to be of a lower frequency than the alternating first frequency. The sense coils are further operated to detect further output signals related to eddy currents generated in the structure. These further output signals are stored. The further drive coil is driven with the second input signal to generate further eddy currents in the structure. Again the sense coils are operated to detect additional output signals related to eddy currents generated in the structure and these additional output signals are also stored. The additional output signals are scaled to the stored further output signals and the scaled additional output signals are then compared with the further output signals for anomalies indicative of defects in an underlying layer of the structure.

The method of the immediate preceding paragraph in a preferred embodiment further includes centering the probe by driving the central core drive coil with the first input signal and operating each of the sense coils to detect initial output signals related to eddy currents generated in the structure. These detected output signals are analyzed for anomalies indicative of the probe being off center from the area being inspected. The method of such embodiment further includes storing the initial output signals detected by each of the sense coils and scaling the stored initial output signals to the stored further output signals. The scaled initial output signals are then compared with the stored further output signals for anomalies indicative of the probe being off-centered from the area being inspected or the probe not being oriented parallel, i.e. tilted or inclined, to the area being inspected.

The method in another preferred embodiment includes calibrating the probe by positioning and centering the probe against a layered structure known to be free of defects and driving the central core drive coil with the second input signal. Each of the sense coils is then operated to detect calibration signals related to eddy currents generated in the structure. These calibrated signals are stored and compared to the additional output signals to determine a scaling factor.

Further in accordance with the objects of this invention, the method includes positioning the probe against a layered structure proximate the area to be inspected and moving the probe though a closed orbit that is centered about an off-centered axis that is parallel to and radially displaced from the central axis of the central core. The central core drive coil is then driven with a signal of an alternating frequency to generate eddy currents in the structure. The sense coils are operated to detect initial output signals related to eddy currents generated in the structure. The detected signals are then analyzed for anomalies indicative of defects in the structure. Movement of the probe in the orbit can be oscillating movement, wherein the probe is moved radially relative to the off-centered axis without rotating the probe about the off-centered axis, or said movement can be rotational movement wherein the probe is rotated about the off-centered axis. In other preferred embodiments, the additional wall is a circumferentially extending wall that is radially displaced from the central core and the sense coils are located in a symmetrical array around this circumferentially extending wall.

Further in accordance with the objects of the invention, a further method of inspecting a layered structure includes selecting a probe having a first body formed of a high permeability material with the first body shaped to include a central core having a core axis and a core drive coil wound on the central core. The probe further includes a further body having a further body central axis and a plurality of independent sense coils located around the further body central axis, with the further body located adjacent to the first body and with the further body central axis located parallel to but radially displaced from the core axis. The probe further includes means for moving said first body in a prescribed closed orbit with respect to the further body. The further method includes positioning the probe against a layered structure proximate the area to be inspected and moving the first body of the probe though a closed orbit that is centered about the further body axis. The core drive coil is then driven with a signal of an alternating frequency to generate eddy currents in the structure, and the sense coils are operated to detect initial output signals related to the eddy currents. The detected signals are then analyzed for anomalies indicative of defects in the layers of the structure. Movement of the first body through the closed orbit can be movement by rotating the first body around the further body axis or it can be movement wherein the first body is oscillated about the further body axis while holding the first body fixed with respect to rotation of the first body about the further body axis.

Further in accordance with this invention, there is provided a structural defect detection system that includes a body formed of a high permeability material. The detection system further includes a plurality of independent drive coils, each of which is independently located on the body and each of which is capable of inducing eddy currents in a metallic structure in response to an AC signal conducted through the drive coils. A plurality of independent transducer means are located in a symmetrical array in operative association with the body. Each of the transducer means is for sensing eddy currents in a structure and producing an output signal in response to said sensed eddy currents. Transducer means are formed independent of the drive coils. The detection system further includes signal generating means for generating at least one selected AC signal of a selected frequency and a drive select means for independently driving one of the drive coils with the selected signal. The detection system further includes a signal processing means operatively associated with the plurality of transducer means for independently processing the output of each of the plurality of transducer means and for producing an output indicative of differences between the output signals of the transducer means. In preferred embodiments the transducer means comprises sensing coils mounted on the body. In further preferred embodiments the signal generating means generates a drive signal and first and second reference signals with at least the second reference signal differing in phase from the drive signal and the first reference signal. The drive select means drives the drive coil with the drive signal, and the signal processing means processes the output signal of each of the transducers in association with both the first and second reference signals and in response thereto generates an output having both a phase and a magnitude component.

Further, in accordance with this invention there is provided a method of detecting defects in a structure that includes selecting a probe having a body formed of a high permeability material and having at least one drive coil located thereon that is capable of introducing eddy currents in a metallic structure in response to an AC signal conducted through said drive coil. Further it includes a plurality of independent transducer means located in a symmetrical array in operative association with the body and where each of the transducer means is capable of sensing eddy currents in a metallic structure and in response thereto producing an output signal. The transducer means are independent of the drive coil. The probe is located in association with the structure. An AC drive signal is generated as are first and second AC reference signals. At least the second reference signal differs in phase from the drive signal and the first reference signal. The drive coil is driven with the drive signal to induce eddy currents in the structure. The transducer means are interrogated for transducer output signals produced in response to eddy currents in the structure. The output signal of each transducer means is processed in association with both the first and second reference signals and in response thereto a multiple component output signal is generated that has both a phase and a magnitude component. The phase and magnitude components of the multiple component output signal for each of the transducer means is compared to detect defects in the structure.

BRIEF DESCRIPTION OF THE DRAWINGS

This invention will be further understood when taken in conjunction with the drawings wherein:

FIG. 11 is a pictorial view of a further probe of this invention;

FIG. 12 is a side elevational view in cross section of the probe of FIG. 11;

FIGS. 13, 14 and 15 are pictorial views of portions of probes of the invention;

FIG. 16 is a pictorial view of a portion of a probe of the invention;

FIG. 17 is an isometric view of a further probe of the invention;

FIG. 18 is an isometric view of even a further probe of the invention;

FIG. 26 is block diagram showing the steps of a detection method of the invention;

DESCRIPTION OF THE PREFERRED EMBODIMENTS

Figure 1:
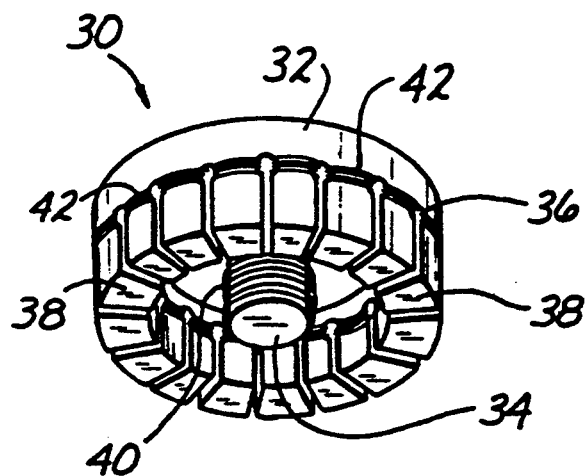
FIG. 1 is a pictorial view of a prior art probe.

Aircraft are typically constructed by fastening a multiple layer skin to underlying structures utilizing fasteners. This design results in thousands of fastener holes located in the hidden underlying structures. Fatigue cracks frequently initiate at such fastener holes. An inspection of the area immediately around each hole is necessary to find such fatigue cracks. Locating fatigue cracks is paramount to flight safety of the aircraft.

While ultrasonic methods are useful for detecting fatigue cracks in a top layer of a layered structure, they are useless for underlying layers. Radiographic detection and conventional eddy current detection will only detect cracks after they have grown to a size that is costly and difficult to repair. Indeed it has been shown that radiographic methods will not detect fatigue cracks until they have propagated across, as for instance, an entire spar and have developed a significant width. Fastener removal to detect cracks utilizing probes that go into the fastener holes is a difficult and expensive task and in itself can result in damage to the structure.

As a design criteria, detection of cracks that are 0.1 inch (2.5 mm) in length in an underlying layer of an aircraft structure having a 0.25 inch (6.35 mm) top layer, as for instance a 0.25 inch (6.35 mm) aluminum skin, utilizing either steel, titanium, or aluminum fasteners is desirable. Further, such inspection should be straightforward, not require highly technically trained personnel, and should be able to be accomplished at a fairly rapid inspection rate.

In accordance with this invention such design characteristics can be achieved and an inspection rate of 30 seconds or less per fastener hole has been demonstrated. Cracks can be detected when they are of such a small size that they can be removed by drilling out the fastener hole and installing an oversized fastener. Further, crack detection can be effected utilizing ferromagnetic and non-ferromagnetic fasteners in, at least, aluminum over aluminum, titanium over aluminum, titanium over titanium, composite over titanium, and composite over aluminum airframe structures. Such detection is effected utilizing eddy currents induced in a top layer, if that top layer is metallic, and the bottom layer of metallic structural components of aircraft frames, wing assemblies, tail assemblies and the like. Further, such inspection has been achieved on structural components that have near-by edges or surfaces and fastener features which in themselves cause disruption of the eddy current and therefore an interfering signal.

In one embodiment of this invention, this invention comprises an improvement to the probe system as described by Lakin in U.S. Pat. No. 4,495,466. As such, the entire disclosure of U.S. Pat. No. 4,495,466 is herein incorporated by reference. As is common with Lakin, in this invention flaws are detected by their perturbation of eddy currents. The perturbation of induced eddy currents cause changes in the associated magnetic flux. The change in the magnetic flux is then detected by a probe.

Contrary to U.S. Pat. No. 4,495,466, the probes of this invention utilize multiple drive coils that allow for detection of structural features such as nearby edges, surfaces, and fastener features that in themselves cause disruption of the eddy currents and therefore produce interfering signals. U.S. Pat. No. 4,495,466 did not include such multiple drive coils and thus lacked the ability to detect interfering structural features such as nearby edges, surfaces and fastener features.

Shown in FIG. 1 is a probe of U.S. Pat. No. 4,495,466. The probe is identified by the numeral 30. The probe 30 includes a core body 32 having a center core 34 and a plurality of key hole shaped openings 36 which define what Lakin refers to as cup core segments 38. A center coil 40 is wound about the center core 34. A plurality of sense coils collectively identified by the numeral 42 are wound between the openings 36 such that each of the cup core segments 38 has a sense coil 42 wound around its base.

Figure 2:
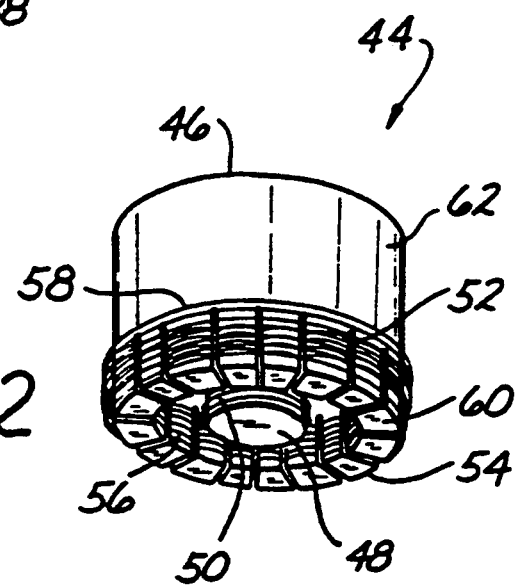
FIG. 2 is a pictorial view of a probe of this invention.

FIG. 2 is illustrative of a probe of this invention. In FIG. 2 the probe 44 is formed of a body 46 that includes a central core 48 having a central core drive coil 50 wound thereon. A plurality of straight sided crenelated openings 52 in the rim 60 of a circumferentially extending wall 62 of the body 46 define a plurality of partitions 54 each of which has an independent sense coil 56 wound thereon. Further, an outer drive coil 58 is wound around the rim 60 of the body 46 radially outwardly from the independent sense coils 56.

The crenelated openings 52 form a castellated like structure in the rim 60. This leaves the partitions 54 with a prismatic like shape having straight walls and a truncated pie like shape in cross section.

The body 46 is formed of a high permeability material, as for instance, a ferrite material. The central core drive coil 50 and the outer drive coil 58 are completely independent of each other. Further, the independent sense coils 56 are independent of each other as well as being independent of the central core and outer drive coils 50 and 58.

Figure 3A:
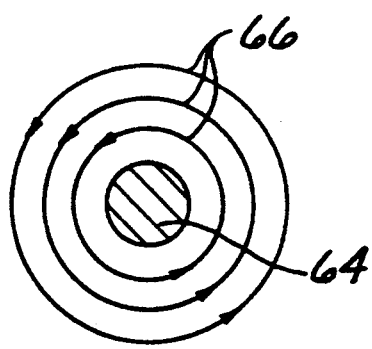
FIG. 3a is representational view of eddy currents surrounding a cross section of a fastener located in a structure and FIG. 3b is a similar representational view and in addition includes a crack located in the structure.
Figure 3B:
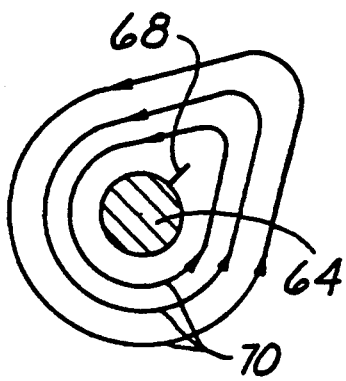

In FIGS. 3a and 3b, operation of the probe 30 of U.S. Pat. No. 4,495,466 and those features of the probe 44 of this invention that are in common with U.S. Pat. No. 4,495,466 are illustrated.

In FIG. 3a is shown that, when the central core of a probe, as for instance the center core 34 of the probe 30 of U.S. Pat. No. 4,495,466, or the central core 48 of the probe 44 of this invention, is located over a fastener 64 and an alternating current is passed through the coil that surrounds the central core of the probe, eddy currents, as are illustrated by the lines 66 in FIG. 3a, are generated in the metallic structure in which the fastener 64 is located. The magnetic flux generated by the current flowing through the coil that surrounds the probe core induces the eddy currents 66 in the metallic structure.

As illustrated in FIG. 3b, when a defect, as for instance a crack 68, is located in the structure adjacent to the fastener 64, the eddy currents as are illustrated by lines 70 of FIG. 3b, are perturbed by the presence of the crack 68 and this in turn perturbs the magnetic flux associated with those eddy currents.

In both the probe 30 of U.S. Pat. No. 4,495,466 and the probe 44 of this invention, the sense coils of the probe are sensitive to the magnetic flux. Current is induced in the sense coils in response to changes in the magnetic flux. The perturbance of the magnetic flux caused by the crack 68 is sensed by the sense coils as these sense coils measure the spatial distribution of current around the fastener 64. Flaws are detected as perturbations in the current distribution.

If fasteners were simply positioned in structures that were essentially infinitely large with respect to the fastener geometry such that other parts of the structures did not affect the eddy current distribution around a fastener, probes such as the probe 30 of U.S. Pat. No. 4,495,466 would be very effective in sensing defects such as the crack 68. In actuality, however, especially with respect to aircraft formed of composite structures, the underlying or second layer through which a fastener also passes generally has geometry or special features that interfere with the idealized circular distribution of eddy currents as shown in FIG. 3a.

Figure 4:
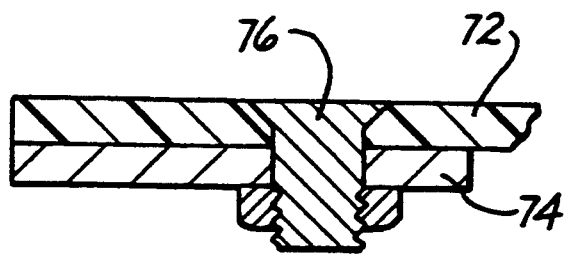
FIG. 4 is a side elevational view of a layered structure having a fastener therein.
Figure 5:
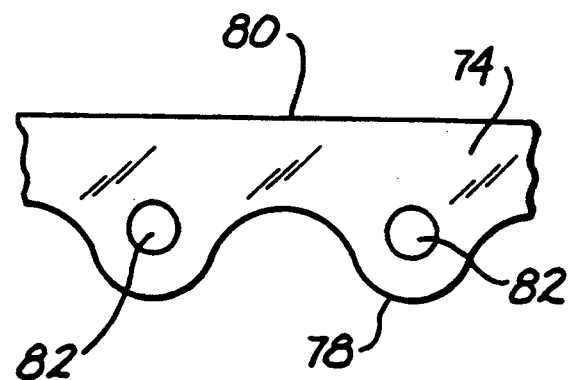
FIG. 5 is a top plan view of the bottommost layer of the structure of FIG. 4.

As is illustrated in FIG. 4, a composite outer skin 72 has been layered on an aluminum spar 74 and held in place with a fastener 76. In FIG. 5 the spar 74 is isolated. As can be seen, the spar 74 includes a scalloped side 78 and a straight web side 80. Fastener holes collectively identified by the numeral 82 are positioned closer to the scalloped side 78 than they are to the straight web side 80. By itself, the geometry around the fastener holes 82 is sufficiently different between the scalloped side and the straight web side to perturb the eddy current around the fastener holes 82. Probes such as the probe 30 of FIG. 1 of U.S. Pat. No. 4,495,466 are unable to differentiate between cracks around the fastener holes 82 and the complex geometry of the spar 74.

Figure 6:
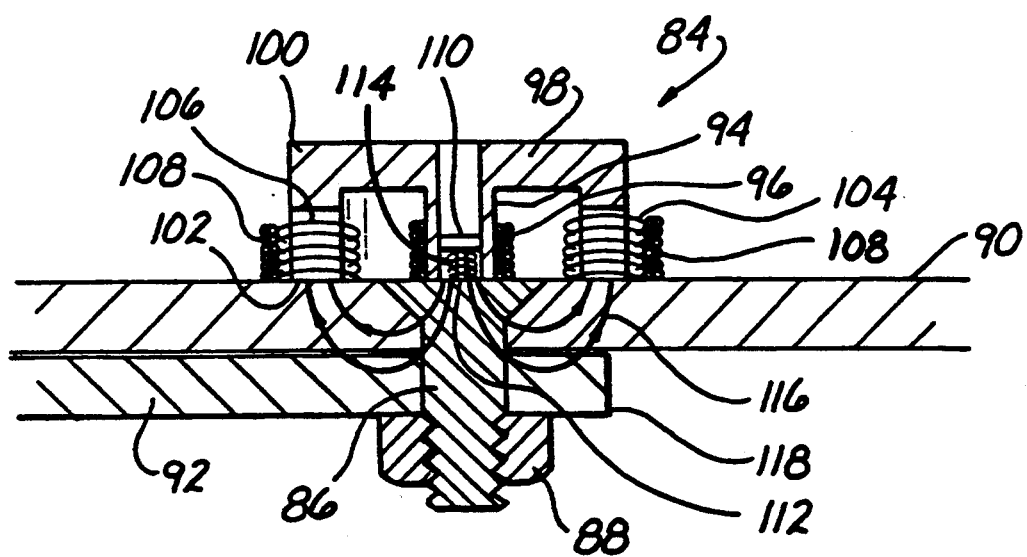
FIG. 6 is a side elevational view in cross section of a probe of the invention and a layered structure having a fastener therein.

A representational probe 84 of the present invention is illustrated in FIG. 6. The probe 84 has many things in common with the probe 44 of FIG. 2 and in addition thereto it has other features. The probe 84 is located over a fastener 86. In conjunction with a nut 88, the fastener 86 holds a first layer 90 and a second layer 92 of a layered structure together. It can be seen that the second layer 92 is of a different geometry than is the first layer 90. Thus, eddy currents to the right side of the fastener 86, as viewed in FIG. 6, would be different than those to the left side of the fastener 86 as viewed in FIG. 6.

The probe 84 includes a central core 94 around which is wound a central core drive coil 96. A radially extending wall 98 radially extends from the central core 94 outwardly and joins a circumferentially extending wall 100. The circumferentially extending wall 100 includes a rim 102 that rests against the top of the first layer 90. The rim 102 is castellated as is described for the probe 44 of FIG. 2 to form individual partitions around its circumference. Sense coils 104 and 106 are located around two of these partitions on the rim 102 of the circumferentially extending wall 100. Of course, not seen in FIG. 6 are other partitions each having its own sense coil as is illustrated in FIG. 2. Radially outward from the sense coils 104 and 106 is an outer drive coil 108. The central core 94 of the probe 84 is hollow and includes a central body 110 located therein. Central body 110 has a boss 112 around which is wound a central body coil 114.

When current (an input signal) is passed through the central core drive coil 96, magnetic flux lines 116 penetrate the first and second layers 90 and 92, and if these layers are metallic, introduce eddy currents therein. For the structure of FIG. 4, only a small amount of eddy currents would be generated in the composite outer skin 72 since it is not metallic. However, significant eddy currents would be generated in the aluminum spar 74 since it is metallic. Assuming for illustrative purposes that both the first and second layers 90 and 92 of FIG. 6 are metallic, the magnetic flux lines 116 would generate eddy currents in both of these layers. In turn, these eddy currents would be sensed by the sense coils 104 and 106 and other sense coils which extend around the circumference of the rim 102 of the circumferentially extending wall 100.

It is evident from FIG. 6 that the magnetic flux in the second layer 92 would be quite different on the right hand side of fastener 86 than on the left hand side of the fastener 86 because of the presence of the edge 118 of the second layer 92 in this area. Sense coil 104 would therefore see a different eddy current environment within the second layer 92 than sense coil 106 simply because of its spatial position. This difference, however, would not be indicative of a crack in the second layer 92, but simply would be indicative of the geometry of the second layer 92.

Utilizing the probe 84 of this invention, the perturbations of the eddy currents in the second layer 92 can be differentiated from those caused by cracks and other defects by independently probing the first and second layers 90 and 92 with a magnetic flux that is generated by activating the outer drive coil 108. The magnetic flux lines that emanate from the circumferentially extending wall 100 in response to driving the outer drive coil 108 are sensitive to the geometry of the layers of the structural material adjacent to these outer drive coils, i.e. the edge 118, but not to the fastener 86, since the fastener 86 is displaced inwardly from the outer drive coil 108.

If measurements are made with the sense coils 104 and 106 and the other sense coils not seen in FIG. 6 in response to eddy currents induced by the outer drive coil 108, these measurements will be indicative of the geometry of the structure being scanned in those areas of this structure that are outwardly from the fastener 86.

If these measurements are then compared to the measurements made when the central core drive coil 96 is driven, and if the two sets of measurements are scaled one to the other, it is possible to remove that part of the output signal that is generated by the structural geometry such that signal indicative of cracks and other defects can be differentiated from signal that arises only because of the geometry of the structure being tested. The incorporation of the outer drive coil 108 or other such additional drive coil allows this to be achieved.

FIGS. 7, 8, 9 and 10 show response curves for a probe, as for instance the probe 44 of FIG. 2, which has 16 individual sense coil elements. The vertical axis is indicative of probe response amplitude and the horizontal axis is divided to show the response for each of the individual 16 sense coils. The probe 44 of FIG. 2 has been positioned against a structure, as for instance the structure of FIGS. 4 and 5 that contains a complex geometrical component as its lower component, e.g. the aluminum spar 74 having scalloped side 78 and straight web side 80. For identification purposes, the sense coils of the probe are numbered 1 through 16. The probe has been positioned such that sense coil number 5 is immediately adjacent the scalloped side 78 and sense coil number 13 is immediately adjacent the straight web side 80. The individual responses of the sense coils have been joined to form a rough curve.

Figure 7:
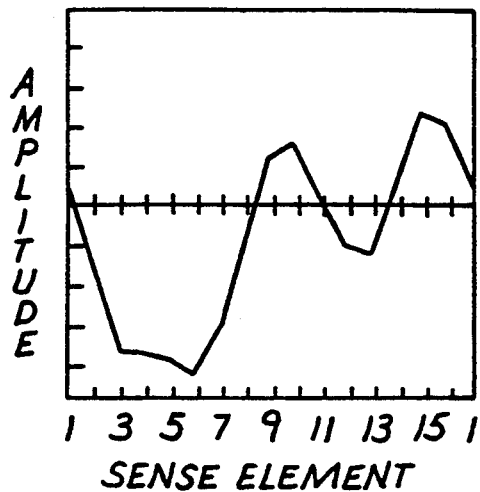
FIGS. 7, 8, 9 and 10 are graphs showing pictorial output displays of signals generated using probes of the inventions.
Figure 8:
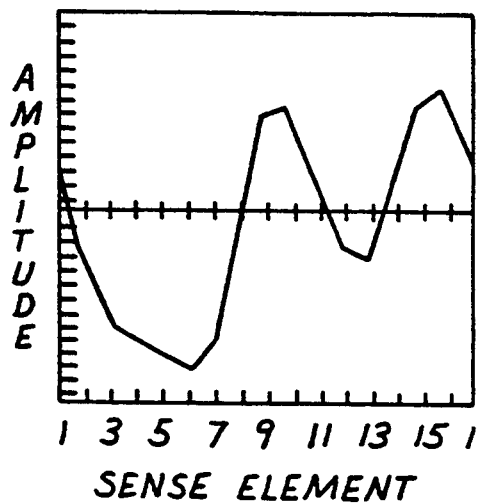

The curve shown in FIG. 7 is that which is obtained when the central core drive coil 50 of the probe 44 is driven with an appropriate AC signal of a selected frequency. The curve shown in FIG. 8 shows the probe response in the same location except in this instance the outer drive coil 58 was driven by this same signal. As is evident in comparing FIGS. 7 and 8, the shape of the curve that is derived by connecting the probe responses is very similar except for a scaling factor. The scale of FIG. 8 is much larger than the scale of FIG. 7. It is also evident that the shape of this curve is somewhat complex, and determining whether or not a crack is present around one of the fastener holes 82 is not immediately evident. Even though they look complex, the response of FIGS. 7 and 8 are illustrative of the response obtained when no crack or other defect is present around a fastener hole in a layered structure of complex geometry.

Figure 9:
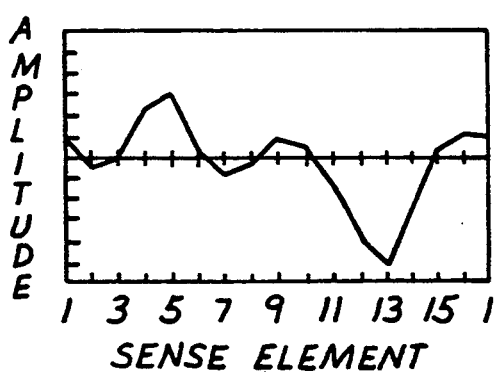
Figure 10:
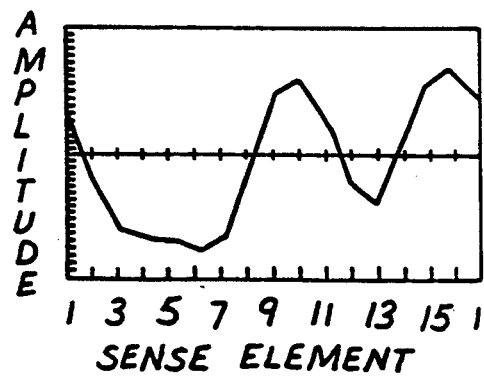

In FIGS. 9 and 10, a similar response to those shown in FIGS. 7 and 8 is measured, except in this case there is a crack adjacent to the fastener hole being tested. FIG. 9 is the response curve that is generated when the central core drive coil 50 is activated and FIG. 10 is the response curve that is generated when the outer drive coil 58 is activated. In this instance the shape of the curves look different around the scalloped side 78, which is generally proximate to the sense coil number 5, compared to that shape around the straight web side 80, which is generally proximate to the sense coil number 13. The curves are generally similar near the straight web side 80, but are different near the scalloped side 78.

From the curve of FIG. 9, by itself, one would not know whether or not one is simply looking at a response that has been generated because of geometry or a response that has been generated because of a defect. However, when one compares the curve of FIG. 9 to the curve of FIG. 10, and utilizes the curve of FIG. 10 to remove the response that is only indicative of geometry of the structure being tested, the presence of a crack adjacent a fastener hole can be determined. It is apparent that, if the curve of FIG. 10 were scaled to that of FIG. 9 and subtracted therefrom, it would be evident that there is a crack positioned adjacent to sense coils 4 or 5.

As per this invention, by placing an outer drive coil near the outside of the probe body, the outer drive coil can be used to generate an eddy current distribution that is sensitive to the boundaries of the structure being tested, but not small flaws near fastener holes being tested. Measurements taken when driving this outer drive coil are then used to remove the effects of the boundary variations from the measurements taken when driving the central core drive coil. What is left is a signal indicative of flaws around the fastener hole.

Referring back to FIG. 6, by forming the central core 94 of the probe 84 body as a hollow core, the probe 84 can be utilized to inspect the area around steel fasteners. By utilizing a hollow central core, eddy currents generated in steel fastener heads are limited. This in turn provides for greater sensitivity to flaws around the fastener hole. A further advantage can be achieved by placing a further core body, central body 110, into the hollow central core 94. Activation of the central body coil 114 directly over a steel fastener allows for convenient centering of the probe 84 over such a steel fastener. By driving the central body coil 114, an eddy current is generated in the fastener head which is sensed by the sense coil array. By moving the probe 84 until the signal sensed by the individual sense coils is approximately equal, convenient centering of the probe 84 over a fastener is achieved.

FIGS. 11 through 16 are illustrative of a further embodiment of this invention. In this embodiment a probe 120, seen in FIGS. 11 and 12, is formed of a first body 122 that has a central core 124, a radially extending wall 126, and a circumferentially extending wall 128 essentially as illustrated for the probe 84. A central core drive coil 130 is wound around the central core 124 and an outer drive coil 132 is wound around the circumferentially extending wall 128. The rim of the circumferentially extending wall 128, however, is not partitioned or castellated as per the prior probes 44 or 84. Instead, it terminates in a solid lip 134. A further body 136 is mounted on the lip 134. In FIGS. 11 and 12 the further body 136 is simply shown as a generic body and the sense elements or sense coils that are associated with it are not illustrated. Preferably the first body 122 of the probe 120 is formed of a high permeability material, as for instance a ferrite material. The further body 136, however, need not be formed of such ferrite material and can be formed of a material more easily worked, as for instance, a resin or the like.

In FIG. 11, for illustrative purposes, a series of phantom lines, collectively identified by the reference numeral 138 are shown dividing the further body 136 into a plurality of segments. These segments are symmetrically arrayed with respect to the central core 124. As is further illustrated in FIGS. 13 through 16, transducers are located in each of the segments defined by the phantom lines 138. Thus, there is a circumferential symmetry around the further body 136 with respect to the central core 124. This symmetry is analogous to the symmetry as is illustrated in the probe 44 of FIG. 2 for the plurality of partitions 54 and sense coils 56 that are part of the structure of the probe 44.

In FIG. 13, the further body 136 includes a plurality of sense coils collectively identified by the reference numeral 140. Each of the sense coils 140 is wound around an associated ferrite core 142. The ferrite cores 142 are simply small segments of ferrite rod that are easily obtained by segmenting an appropriate ferrite rod into appropriate sections. The sense coils 140, wound around their ferrite cores 142, are embedded in a resin matrix 144 to form one embodiment of the further body 136. In the embodiment of FIG. 13, the axes of the sense coils 140 are parallel to and radially displaced from the axis of the central core 124 when the further body 136 is mounted onto the first body 122. The sense coils 140 and their associated ferrite cores 142 are circumferentially arranged in a symmetrical array within the resin matrix 144 such that they form a symmetrical array within the further body 136 when mounted on the first body 122. Each of the sense coils 140 and its associated central ferrite core 142 are appropriately located in one of the segments that are defined by the phantom lines 138.

Referring now to FIG. 14, a plurality of sense coils 146, each of which has an associated ferrite core 148, are located in a resin matrix 150 as with the embodiment of FIG. 13. However, and contrary to the embodiment of FIG. 13, the axes of the sense coils 146 and their ferrite cores 148 in the embodiment of FIG. 14 lie in a plane that is perpendicular to the axis of the central core 124 of the first body 122. As with the embodiment of FIG. 13, each of the sense coils 146 of FIG. 14 is located in one of the segments that are defined by the phantom lines 138 of FIG. 11.

In FIG. 15 a further embodiment of the invention is illustrated. In this embodiment, the sense coils are spaced apart the same arcuate distance with respect to the central core 124 but are positioned at different radial dimensions from the central core 124. In the embodiment of FIG. 15, an array of outer sense coils 152 form an outer circular symmetrical array and a further array of inner sense coils 154 form an inner circular symmetrical array. For ease of illustration of the FIG. 15, ferrite cores have not been included in the sense coils 152 and 154 of FIG. 15. However, such ferrite cores could easily be incorporated therein. The sense coils will operate with or without ferrite cores. Use of ferrite cores is preferred for the outer circular symmetrical array of outer sense coils 152.

In positioning the outer and inner sense coils 152 and 154, an outer sense coil 152 is placed in one of the segments defined by the phantom lines 138 of FIG. 11, and then an inner sense coil 154 is placed in the next adjacent segment alternately around the circumference of the probe 120.

In use, the outer circular symmetrical array of outer sense coils 152 is operated independently from the inner circular symmetrical array of inner sense coils 154, since they experience different magnetic flux environments when probe 120 is utilized to sense a fastener hole in a structure.

In FIG. 16 a further embodiment of the probe 120 of FIG. 11 is illustrated. In this embodiment, the further body 136 is formed as a monolithic body 156 having a plurality of Hall effect sensors 158 formed therein. The Hall effect sensors are integrally formed within monolithic body 156 utilizing appropriate integrated circuit device construction techniques. When so formed, the monolithic body 156 is very thin, since the Hall effect sensors are formed on the surface of such a monolithic body. In operation, the Hall effect sensors 158 operate in a manner analogous to the sense coils described for the other embodiments.

In FIGS. 17 and 18 further embodiments of the probe of the invention are illustrated. In FIG. 17, a first linear probe 160 is illustrated. The first linear probe 160 has a first solid elongated section identified by the numeral 162. First solid elongated section 162 has a first side 164 and a second side 166. First drive coil 168 is wrapped around first solid elongated section 162 in the elongated dimension of first solid elongated section 162 between the first and second sides 164 and 166. A plurality of individual first partitions collectively identified by the numeral 170 extend along the first side 164. Each of the first partitions 170 is spaced apart from the others and is oriented essentially perpendicular to the first solid elongated section 162. Further, the first partitions 170 are essentially aligned with each other. The first partitions 170 thus form a first array of partitions. In a like manner, a plurality of second partitions 172 are positioned along second side 166. As with the first partitions 170, the second partitions 172 are spaced apart from each other, are oriented essentially perpendicular to the first elongated section 162, are essentially aligned with each other, and form a second array of partitions.

A plurality of sense coils collectively identified by the numeral 174 are wound around the second partitions 172 such that each second partition 172 has a sense coil 174 wound around it. The sense coils 174 are independent of each other and are further independent of the first drive coil 168. A further drive coil 176 is wound around the periphery of the first elongated section 162 encompassing the first side 164 and the second side 166. The first linear probe 160 is operated in an equivalent manner to the above described circular probes 44, 84, and 120. The probe geometry selected for an inspection, i.e. circular or linear, depends upon the geometry of the region to be inspected. In choosing between circular or linear probes, the probe geometry is selected such that, when an eddy current is generated by the probe and distributed in the part to be inspected, the eddy current pattern is consistent with the geometry of the region to be inspected and the geometry of anticipated flaws in the region.

In FIG. 18 a further embodiment of the linear probe of FIG. 17 is illustrated. In this FIG. 18, a second linear probe 178 includes the features of the first linear probe 160 and further includes a second solid elongated section 180 that is joined to the first solid elongated section 162 at the second side 166 of the first elongated section 162 as described for FIG. 17. A plurality of individual third partitions, collectively identified by the numeral 182, extend in a linear array along the outer side 183 of the second solid elongated section 180 opposite from the first solid elongated section 162 and the second array of partitions 172. Like the partitions of the pluralities of the first and second partitions 170 and 172, the third partitions 182 are spaced apart from each other, are oriented essentially perpendicular to the joined first and second solid elongated sections 162 and 180, and are essentially aligned with each other. The sense coils 174 wound around the second partitions 172 are thus disposed on the center array of the second linear probe 178. A second drive coil 184 is wrapped around the second solid elongated section 180 in the elongated dimension of second solid elongated section 180 between the second and third arrays of partitions and encompassing the first side 164 and the outer side 183.

Figure 19:
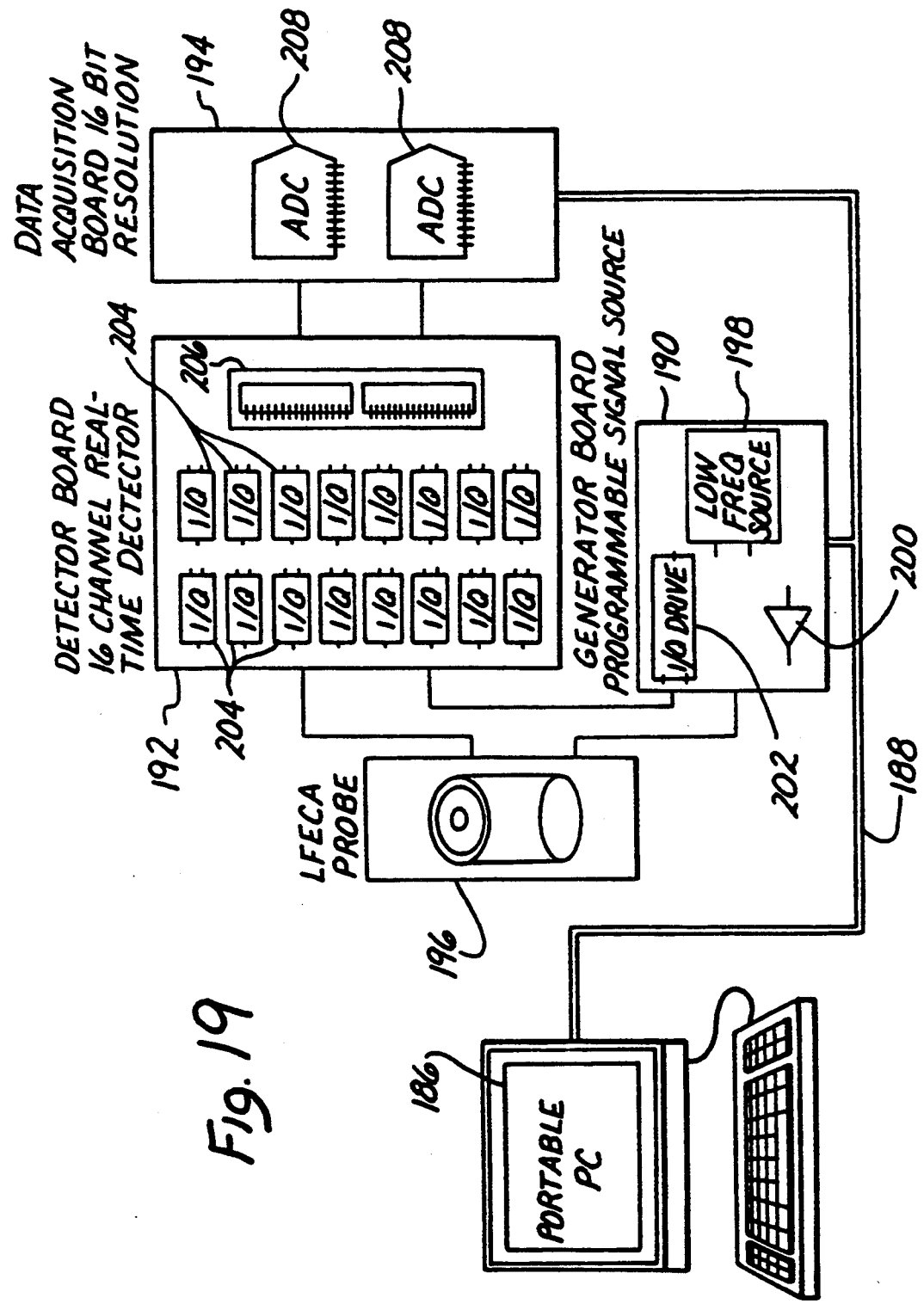
FIG. 19 is a synoptic diagram of a detection system of the invention.

FIG. 19 shows a synoptic diagram of the electronics associated with the probes of the invention. Illustrated in FIG. 19 is a portable personal computer (PC) 186 and three boards which are inserted in appropriate peripheral slots of the computer 186. The boards connect on the internal bus of the computer 186, identified as computer bus 188. The first of these boards is a generator and programmable signal source board 190. The second board is a 16 channel quadrature detection board 192, and the third board is a data acquisition board 194. Also connected to this system is a probe of the present invention identified as probe 196. The probe 196 can be any of the above described probes.

In use, the probe 196 is appropriately positioned over a fastener to be tested, and the operator enters an appropriate command in the computer 186 such that a signal is generated on the signal source board 190 and is used to drive the probe 196. Output signals of the sense coils of the probe 196 are directed to the quadrature detection board 192 for detection and from there to the data acquisition board 194 for conversion into digital form for introduction back onto the computer bus 188 for appropriate read out on the computer 186.

The signal source board 190 includes a low frequency source means 198, an amplifier means 200, and a drive means 202. The low frequency source means 198 is utilized to generate an appropriate AC signal of a selected frequency. This signal is amplified by the amplifier means 200 and directed via the drive means 202 to an appropriate drive coil in the probe 196.

Each of the sense coils of probe 196 are connected to an independent quadrature detection means, collectively identified by the numeral 204, on the quadrature detection board 192. Outputs from the independent quadrature detection means 204 are directed to a multiplexer means 206, also on the quadrature detection board 192. First and second detected outputs, as are described below, are fed to standard analog to digital converter means, collectively identified by the numeral 208 on the data acquisition board 194. Digital signal is then fed back from the analog to digital converter means 208 onto the computer bus 188 for analysis and display by the computer 186.

Figure 20:
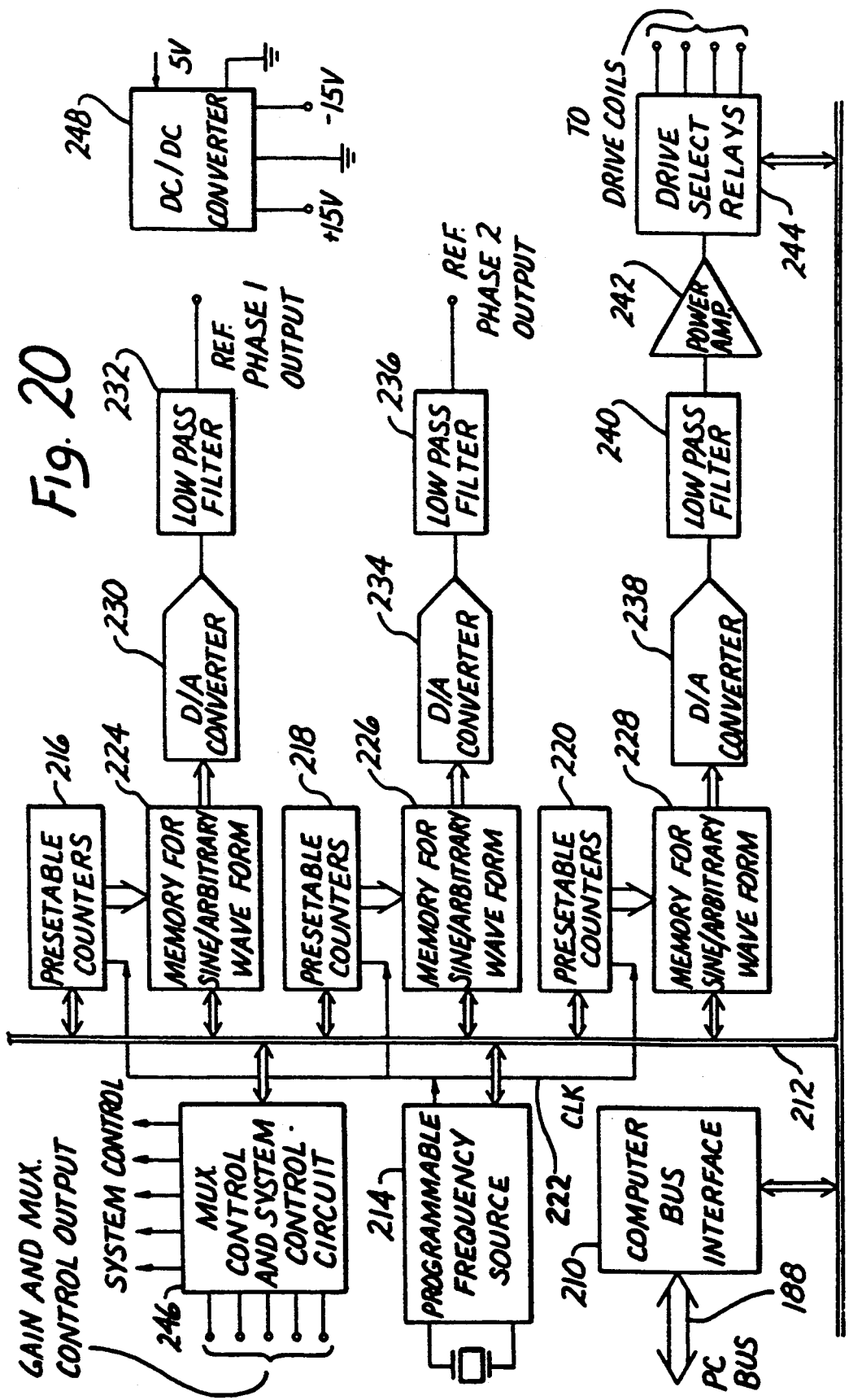
FIG. 20 is a simplified schematic block diagram illustrating in greater detail portions of the system of FIG. 19.

The signal source board 190 of FIG. 19 is shown in greater detail in FIG. 20. A computer bus interface means 210 connects to the computer bus 188 of FIG. 19. This computer bus interface means 210 connects an internal board bus 212 to the computer bus 188. The signal source board 190 further includes a programmable frequency source 214. An appropriate signal of a chosen frequency from the programmable frequency source 214 is independently sent on the internal board bus 212 to first, second and third pre-setable counters 216, 218 and 220, respectively. A clock signal from the programmable frequency source 214 is further sent on clock line 222 to the first, second, and third pre-setable counters 216, 218, and 220.

Associated respectively with the first, second, and third pre-setable counters 216, 218 and 220 are first, second, and third memory units, each for storing a selected wave form, as for instance, a sine wave form. These associated memory units are respectively identified in FIG. 20 by numerals 224, 226 and 228. They can be selected as EPROMS, ROMS or other suitable IC devices for storing preselected wave forms. A first signal of a selected preset frequency and wave form is fed from the first memory unit 224 to a first digital to analog (D/A) converter 230 and then to a first low pass filter 232 for generation of a first reference output signal of a known and pre-selected phase. In a like manner, a second signal of a selected preset frequency and wave form from second memory unit 226 is fed through second D/A convertor 234 and second low pass filter 236 for generation of a second reference output signal of known frequency and phase.

Generally, the second reference output signal would be of the same frequency and amplitude as the first reference output signal, except that it would be out of phase with the first reference output signal, as for instance by 90°. For example, the first reference output signal from first low pass filter 232 would be a sine wave signal, while the second reference output signal from second low pass filter 236 would be a cosine wave signal (i.e. 90° out of phase with the first reference output signal).

In a like manner, a third signal of a selected frequency and wave form from the third memory unit 228 is fed through third D/A converter 238 and third low pass filter 240. This signal, however, is passed through power amplifier 242 and then to a drive select relay means 244. Together the components 214 through 240 comprise the low frequency source means 198 of FIG. 19. The power amplifier 242 comprises the amplifier means 200 and the drive select relay means 244 comprises the drive means 202.

Also located on the signal source board 190, as is seen in FIG. 20, is a multiplexer and system control module 246 that controls gain and multiplex selection of the quadrature detection board 192 as is described in detail below. Further, the multiplexer and system control module 246 controls the output signal of the data acquisition board 194. Additionally, located on the signal source board 190 is a DC power source 248 for the quadrature detection board 192.

In summary, the features of the signal source board 190 are that it generates three channels of sine wave output (or other selected wave form) with software control of the phase of all three output channels and control of the magnitude of the output channel provided to drive select relay means 244 through the power amplifier 242. Frequency is also under software control and can range from 20 Hz to 20 kHz in appropriate steps. The output from the power amplifier 242 is directed, via the drive select relay means 244, to the various drive coils of the probe, as for instance the central core drive coil 96, the outer drive coil 108, or the central body coil 114 as described for the probe 84 of FIG. 6 above. Selection of output to a drive coil is also under software control via the drive select relays means 244 and input from the computer 186 via the computer and internal board busses 188 and 212. Finally, power supply voltage for the quadrature detection board 192 is provided by the power source 248.

The quadrature detection board 192 is connected via appropriate cables to the probe 196. The quadrature detection board 192 is a 16 channel board and each particular channel is connected to an associated individual sense coil in the probe 196. Each channel amplifies the associated sense coil's low frequency output, multiples it by quadrature phase components and low pass filters the output. The output of each channel comprises two DC signals representing quadrature components of the associated sense coil's output. The outputs of these channels are multiplexed under software control as follows.

Figure 21:
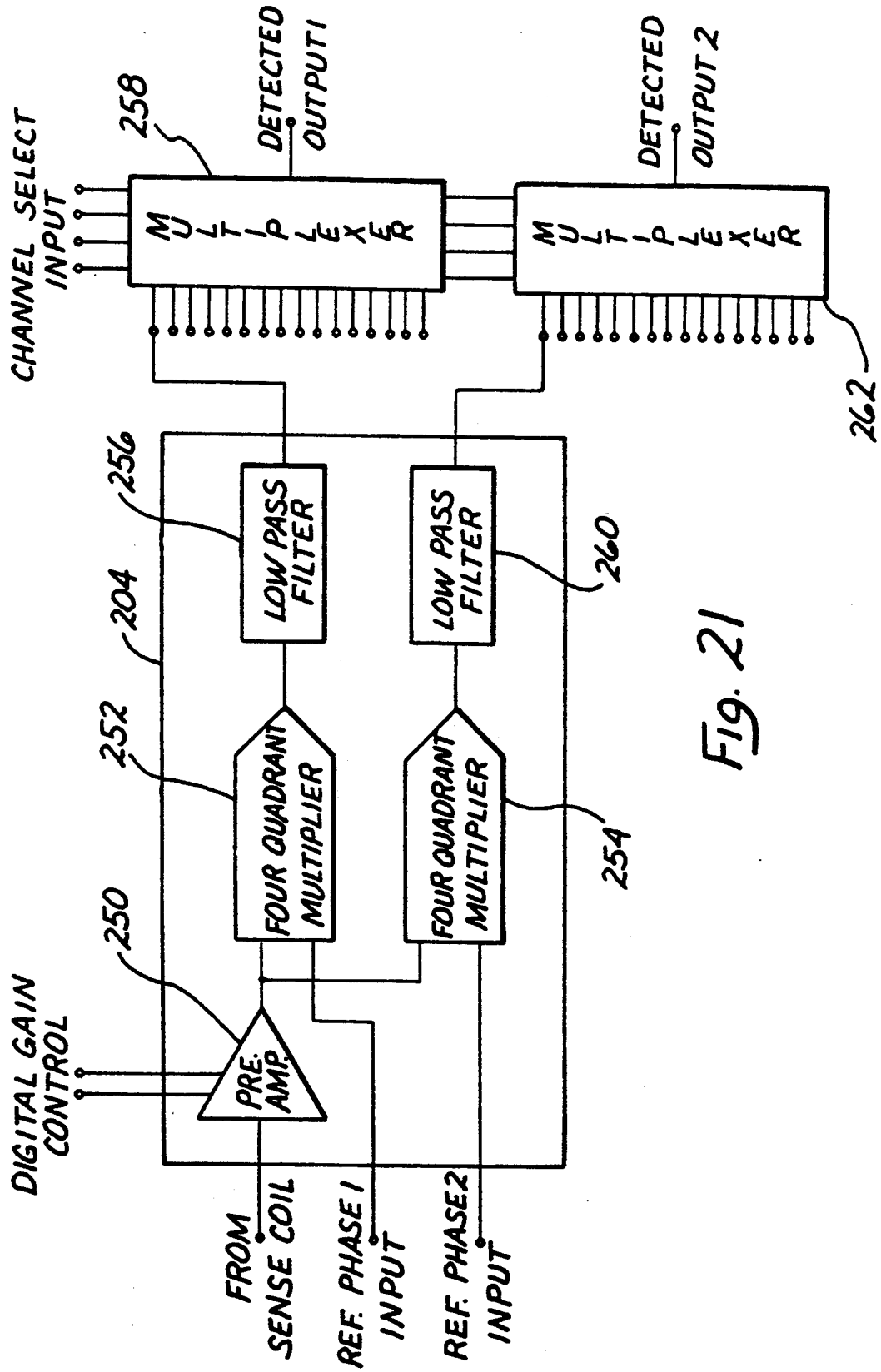
FIG. 21 is a simplified schematic block diagram illustrating in greater detail further portions of the system of FIG. 19.

Shown in FIG. 21 is one of the 16 independent quadrature detection means 204 seen in FIG. 19. Output from a sense coil is directed to a pre-amp 250 that is under the control of the multiplexer and system control module 246 on the signal source board 190. Output from the pre-amp 250 is fed to a first four quadrant multiplier 252 that also receives the first reference output signal from the first low pass filter 232 on the signal source board 190. Output from the pre-amp 250 is also fed to a second four quadrant multiplier 254 that additionally receives the output of the second low pass filter 236, i.e. the second reference output signal that is out of phase with respect to the first reference output signal. Output from the first four quadrant multiplier 252 is fed through a first output signal low pass filter 256 and from there to a first output signal multiplexer 258. Output from the second four quadrant multiplier 254 is fed through a second output signal low pass filter 260 and from there to a second output signal multiplexer 262.

Together the first and second output signal multiplexers 258 and 262 comprise the multiplexer means 206 on the quadrature detection board 192. Output signals from each of the other independent quadrature detection means 204 associated with the sense coils of the probe 196 are in a similar manner directed to the first and second output signal multiplexers 258 and 262. The signal processing of the first and second output signal multiplexers 258 and 262 is under control of the multiplexer and system control module 246 on signal source board 190 as seen in FIG. 20. The first detected output from the first output signal multiplexer 258 is input to a first module of the analog to digital convertor means 208 on the data acquisition board 194 and the second detected output from the second output signal multiplexer 262 is input to a second module of the analog to digital convertor means 208 on the data acquisition board 194. After conversion to digital form, the first and second detected output signals are then fed to the computer bus 188 for appropriate processing and display on the computer 186.

In summary, in FIGS. 19, 20, and 21 is illustrated a structural defect detection system that includes an appropriate probe, as described above, operating in conjunction with a signal generating means for generating at least one selected AC signal of a selected frequency and wave form. A drive selection means propagates the signal to a selected one of the independent drive coils of the probe. A signal processing means associated with the transducer detection means of the probe independently processes the output signal of each of the plurality of transducer means and produces an output thereof that is indicative of the differences in the output signals of the plurality of transducer means.

As illustrated in the probes above, the transducer means preferably comprises sensing coils or Hall effect sensors. Further, as discussed above with respect to FIGS. 19-21, the signal generator means generates a drive signal and first and second reference signals with at least the second reference signal differing in phase from the drive signal and the first reference signal. The drive signal can also differ from the first reference signal, as for instance, being 45° out of phase. Thus, the first reference signal would be a zero phase signal, e.g. a sine signal, the drive signal a 45° phase drive signal and the second reference signal a 90° phase drive signal, e.g. a cosine signal.

The drive select means drives a selected drive coil with the drive signal and the signal processing means processes the output signal of each transducer in association with both the first and second reference signals and in response thereto generates an output. This output, by utilizing the independent quadrature detection means of the quadrature detection board 192, has both a phase and a magnitude component.

In general, the invention as is described in FIGS. 19, 20, and 21, utilizes a method for detecting defects in a structure wherein the components of FIGS. 19, 20 and 21 are utilized in conjunction with a probe as described above. The probe is located in association with an area on a structure to be tested. An AC drive signal and first and second AC reference signals are generated with at least the second reference signal differing in phase from the drive signal and the first reference signal. A drive coil is driven with the drive signal to introduce eddy currents in the structure. The sense coils or other transducer means in the probe are interrogated individually for output signals that are produced in response to eddy currents in the structure. These output signals are processed in association with both the first and second reference signals, and in response thereto a multiple component output signal having both a phase and a magnitude component is generated. Comparison can be made of the phase and magnitude components of the multiple component output signal of each of the transducer means to detect defects in the structure.

Figure 22:
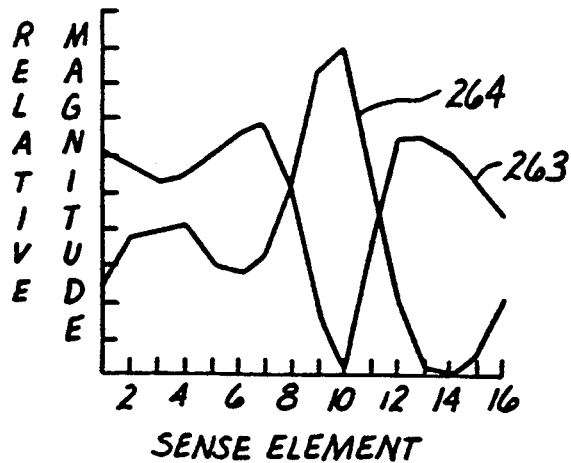
FIGS. 22, 23, 24 and 25 are graphs showing further pictorial output displays of signals generated using probes of the inventions.
Figure 23:
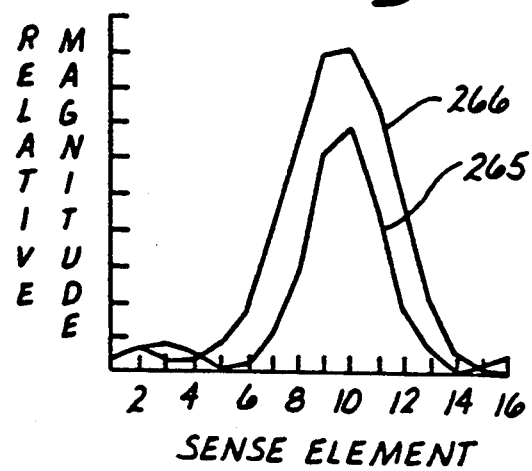

Referring now to FIGS. 22 and 23, the usefulness of both a phase and a magnitude component of the output signal of the independent quadrature detector means 204 of FIG. 19 is illustrated. As with the graphs of FIGS. 7, 8, 9 and 10, the outputs of the individual sense elements of the probe are plotted along the horizontal axis. The vertical axis represents relative magnitude. Both the magnitude and phase are plotted.

First layer signals seen in FIG. 22, which are best produced by utilizing a high frequency signal, have a phase component 263 of a very low relative magnitude and an amplitude component 264 of a high relative magnitude for a first layer defect illustrated in the vicinity of sense element 10. For signals that are indicative of defects in an underlying layer, as is seen in FIG. 23, the amplitude component 265 is of high relative magnitude but, contrary to first layer signals, their phase component 266 is also of a high relative magnitude, for an underlying layer defect illustrated in the vicinity of sense element 10.

Comparison of FIGS. 22 and 23 shows that the relative magnitude of the phase component relative to the magnitude of the amplitude component increases with increasing depth of the defect from the first layer into the second layer. It is thus possible to differentiate the depth of defects around a fastener hole, i.e. whether they are in the first layer or in the second layer, by looking at both the phase and the magnitude components of the signals detected in the individual sense elements.

As is alluded to in the above referenced U.S. Pat. No. 4,495,466, higher frequencies are best suited for detecting cracks in upper layers, whereas it is necessary to utilize lower frequencies for detection of cracks in underlying layers. The programmable frequency source 214 of the signal source board 190 described in FIG. 20 allows for selection of appropriate detection frequencies in a useful range of from about 20 Hz to about 20 kHz. Generally the magnitude of the crack response is proportional to the crack size. Additionally the phase, spectral content, and frequency dependency of the crack response is related in a systematic manner to crack features.

For near surface or first layer cracks, the high frequency response will be sharp and also possess a phase response that identifies it as a near feature crack as is illustrated in FIG. 22. A second layer crack will only be detected in a low frequency response. It will have a broader, less sharper response. Further, the phase response will also indicate the crack as originating from deeper within the structure as is illustrated in FIG. 23.

As a general consideration, the eddy current distribution generated by the central drive coil will not be distributed evenly around the probe. Adjacent structural edges, probe placement and the like will distort the current distribution and will be measured by the probe sense coils. While we do not wish to be bound by theory, it is presently believed that the total probe response can be treated as a linear superposition of these effects. Tilting or lift off of the probe from the surface being checked, as well as having the probe off center from the fastener being checked, do effect crack response, but only to a small degree. It is presently believed that the totality of the probe response is a summation of the crack response, plus the adjacent structure response, plus the off center response, plus the lift off response, plus response related to the fastener itself.

Utilizing the probes and circuitry as described above, those responses that are not crack responses can be eliminated so as to distinguish the crack response from those due to adjacent structure. As described, the geometry of the structure will mask the eddy current response, especially for second layer cracks. Additionally, skin thickness and edge to hole distance influences this response. As was described for FIGS. 7, 8, 9 and 10, use of the outer drive coil with the sense coil array will sense response that is dependent only on adjacent structure and is insensitive to the fastener hole. This response can then be scaled to the response from the center drive coil which is sensitive to the fastener hole. After scaling, the adjacent structure response can then be removed so as to differentiate those responses that are directly the result of cracks from those that are structural responses. Stated in different language, the response to the activation of the center drive coil contains structural inferences as well as crack components, whereas that from the outer drive coil contains only structural inferences that can be scaled and used to remove the response due to structure.

In a like manner, lift off (i.e., where the probe face is perfectly parallel to but raised from the surface being tested), tilt or tilted liftoff (i.e., where the probe face is at an angle to the surface being tested), or off center responses can also be removed. Tilt, lift off, and off center responses are associated with surface features. Probe response for these surface features is predominately generated by eddy currents near the surface. By utilizing a multi-frequency approach, a high frequency measurement is made to isolate near surface effects from those emanating deeper in the structure. Further, tilt, lift off and off center responses have characteristic phase responses. By measuring these at a high frequency they can then be scaled and removed from the response at low frequency since a near linear relationship exists for the scaling of high frequency to low frequency responses. This allows removal of tilt, lift off and off center responses.

Figure 24:
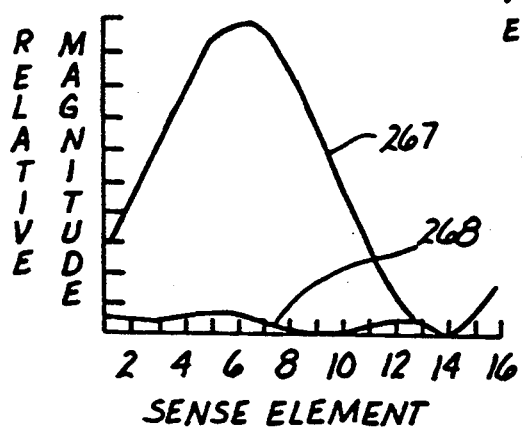
Figure 25:
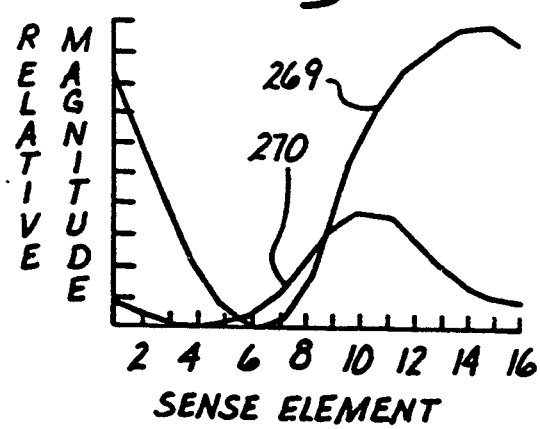

The removal of off center response is illustrated in FIGS. 24 and 25. As with previous graphs, the horizontal axis represents the individual sense elements, while the vertical axis represents the relative magnitudes of sense element outputs. Line 267 of FIG. 24 represents an output without compensation for off centering. When off centering is compensated for, the response line is that shown by line 268. If off center compensation were not made, it would be hard to detect a crack response in the line illustrated by line 267. However, after center compensation is made it is evident from line 268 that there is no crack present. This is compared to FIG. 25 wherein line 269 represents the sense element response prior to centering compensation while line 270 represents that response with centering compensation. Line 270 shows the presence of a crack in the vicinity of sense element 10 that is simply not evident in line 269 because of the off centering response included therein.

Utilizing quadrature detection and plotting on an impedance diagram (in this instance on a pseudo impedance diagram wherein the real component of the response is plotted on the abscissa and the imaginary component of the response is plotted on the ordinate), it will be seen that, for a fastener with no defects, generally all the response will be near the origin. However, if off centering response is present, the real component will vary for the individual sensors more than the imaginary component. In contrast, with tilt or lift off response, the imaginary component varies to a greater degree than the real component. These characteristics allow for identification and removal of erroneous response resulting from either lift off or off centering.

Fasteners can also produce erroneous response. The fastener head may have somewhat of an oval shape, the head pattern could be different, or the fastener hole could be tilted. Responses from such fastener characteristics will generally have phase characteristics of surface features, but will not have spectral responses characteristic of near surface cracks. Changes in countersink angle or over size holes, both of which are symmetrical about the fastener, result in only DC shifts in the probe response and, since they are symmetrical, those shifts do not affect probe response.

Accordingly the following steps, as are illustrated in the flow diagram of FIG. 26, are utilized to segregate the various responses and isolate defects, as for instance cracks in fastener holes. At step 272 of FIG. 26, calibration of the probe is effected by measuring a fastener hole known to be defect free. The probe is then centered at step 274 utilizing a high frequency signal and a real time display at output 276. As was noted above, by utilizing the real component of a quadrature analysis, the probe can be moved until an appropriate real time display shows little variation among the individual sensor responses.

With the probe almost centered at step 278, the center drive is driven with a high frequency signal followed by driving the outer drive coil also with this high frequency signal. Utilizing the techniques as discussed for FIGS. 7 through 10, defects such as a crack under the fastener (CUF) in the first layer can then be seen as a real time output at step 280. At step 282, the center drive coil is driven with a low frequency signal and this output is compared to the high frequency signal output for determination of off centering and liftoff compensation. Since tilt, lift off, and off centering are predominantly surface effects, they are detectable in the high frequency signal and can be removed from the low frequency signal using appropriately scaled high frequency signals. Such compensation is effected at step 284. At step 286, the outer drive coil is driven with a low frequency signal to detect adjacent structure. Such adjacent structure compensation is effected at step 288. Input from the calibration step 272 is then used at step 290 for scaling both the center and outer drive coil responses from an adjacent hole known to be defect free. Upon such scaling, second layer defects are evident at output 292. Having identified the defects, the probe is then moved to the next fastener hole at step 294.

As opposed to utilizing adjacent holes for calibration, the totality of the probe or individual parts thereof can be moved. The current density in eddy currents generated when the center drive coil is driven increase from a position next to the fastener hole to a maximum that is located underneath the body of the probe but away from the fastener hole and then drops to a minimum external of the body of the probe. Advantage can be taken of the maximum current density at a point which is essentially midway between the center drive coil and the outer drive coil.

Figure 27A:
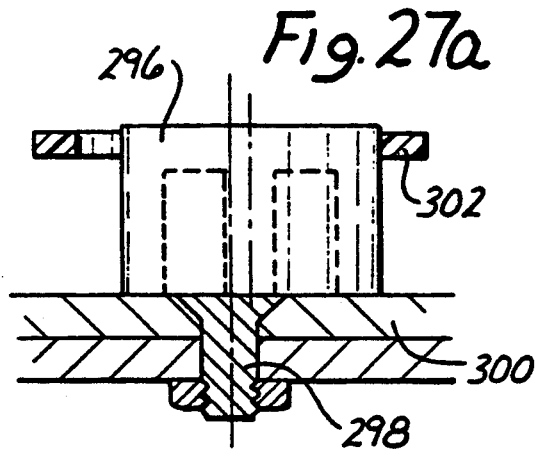
FIG. 27a is an elevational view of a further probe of the invention and FIG. 27b is a plan view schematically showing certain of the components of the probe of FIG. 27a and the paths these components traverse as they move with respect to one another.

As is shown in FIG. 27a, a probe 296 of the invention is located over a fastener 298 that is in a structure 300. The probe 296 fits within a circular guide 302 that has a larger internal diameter than the external diameter of the probe 296. The probe 296 can then be oscillated within the guide 302 by moving the probe in a circular motion within the confines of the guide 302.

Figure 27B:
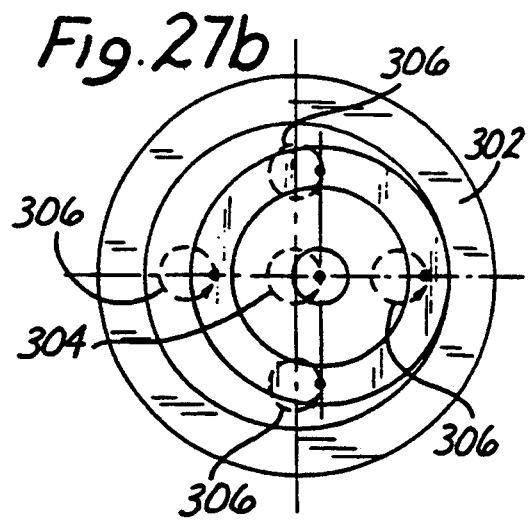

This motion is illustrated in FIG. 27b. In FIG. 27b the path of the center drive coil is indicated by line 304 and paths of representative sense coils by lines 306. The probe is oscillated without rotating it about the center of the probe within the guide 302. The center drive coil and the sense coils are moved through the orbits as illustrated by the lines 304 and 306 of FIG. 27b. The sense coils of the probe thus oscillate, but do not rotate about the center of rotation of the probe itself.

Figure 28A:
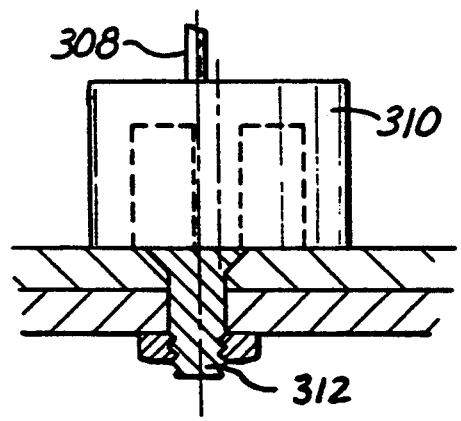
FIG. 28a is an elevational view of an even further probe of the invention and FIG. 28b is a plan view schematically showing certain of the components of the probe of FIG. 28a and the paths these components traverse as they move with respect to one another; and, FIG. 29a is an elevational view of an even further probe of the invention
Figure 28B:
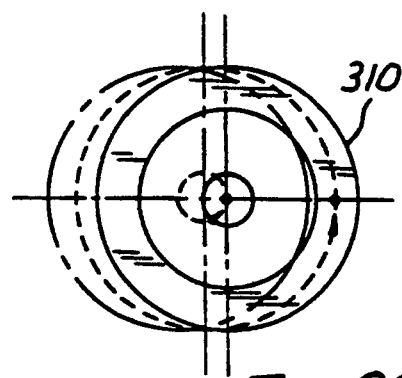

In FIG. 28a a further method of motion is shown. An axle 308 is mounted to a probe 310 off center from the central core of the probe 310. The axle 308 is positioned essentially on center with the center of a fastener 312. The probe is then rotated about the axle 308, which repositions the center drive coil and the sense coils about the axis of the axle 308. The motion path of the off-center rotation is illustrated in FIG. 28b.

Figure 29A:
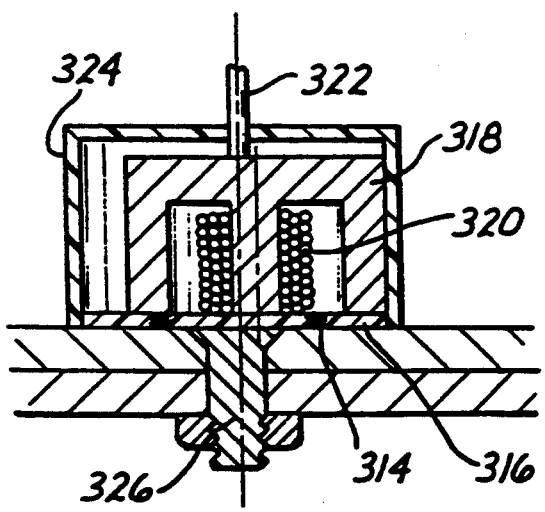
FIG. 29b is a plan view schematically showing certain of the components of the probe of FIG. 29a and the paths these components traverse as they move with respect to one another.
Figure 29B:
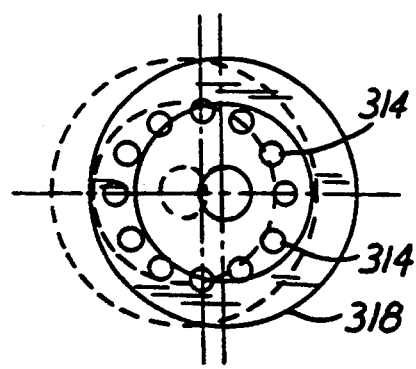

A further embodiment of motion is shown in FIG. 29a. In this embodiment, sense coils 314 are located in a body 316 that is independent of a further body 318 that contains the central drive coil 320. An axle 322 is connected to the further body 318 off center from the central core of the further body 318 and rotates the further body 318 within a case 324 that is mounted to the body 316 along its perimeter. During rotation of the further body 318, the sense coils 314 remain in position. However, the center drive coil 320 is rotated about axle 322 essentially on center with the center of a fastener 326. This is equivalent to the rotation seen in FIG. 28b for the probe 310. However, only the further body 318 of the probe of FIG. 29a, including the central drive coil, is so rotated. The motion path of the off-center rotation of further body 318 is illustrated in FIG. 29b.

In a like manner to that illustrated in FIG. 27b, the center body 318 and its drive coil 320 could be oscillated (but fixed with respect to rotation) around the case 324. In that instance, the axis of the axle 322 is essentially in the center of the body 316, i.e. in the center of the sense coils 314.

This invention may be embodied in other specific forms without departing from the spirit and essential characteristics thereof. The present embodiments are therefore to be construed in all respects as illustrative and not restrictive, the scope of the invention being indicated by the appended claims rather than by the foregoing description and all changes that come within the meaning and range of equivalencies of the claims are therefore are intended to be embraced herein.

What is claimed is:

1. An eddy current probe comprising:

a body formed of a high permeability material, said body being shaped to include a central core and a circumferentially extending wall spaced from and concentric with said central core;

a central core drive coil wound around a surface of said central core facing said circumferentially extending wall, said central core drive coil generating a first magnetic field for inducing central eddy currents in a workpiece upon activation of a flow of alternating current through said central core drive coil;

a plurality of independent sense coils positioned in an array in association with said circumferentially extending wall; and, an outer drive coil wound around an outer surface of said circumferentially extending wall away from said central core, said outer drive coil generating a second magnetic field for inducing peripheral eddy currents in said workpiece upon activation of a flow of alternating current through said outer drive coil, said flow of alternating current through said outer drive coil being activated independently of said flow of alternating current through said central core drive coil, each of said independent sense coils independently sensing respective components of said central eddy currents and said peripheral eddy currents.

2. An eddy current probe comprising:

a body formed of a high permeability material, said body including a central core, a radially extending wall radiating from said central core, and a circumferentially extending wall extending from said radially extending wall concentrically with said central core, said circumferentially extending wall including a rim distal from said radial wall, said rim including a plurality of interstices dividing said rim into a plurality of partitions that are symmetrically located about said rim, said partitions being shaped so as to extend essentially parallel with an axis of said central core;

a central core drive coil wound around a surface of said central core facing said circumferentially extending wall, said central core drive coil generating a first magnetic field for inducing central eddy currents in a workpiece upon activation of a flow of alternating current through said central core drive coil;

a plurality of independent sense coils equal in number to the number of said partitions with a respective one of said independent sense coils being wound around a respective one of said partitions such that each of said partitions includes an associated independent sense coil wound around it; and, an outer drive coil wound around an outer surface of said circumferentially extending wall away from said central core, said outer drive coil generating a second magnetic field for inducing peripheral eddy currents in said workpiece upon activation of a flow of alternating current through said outer drive coil, each of said independent sense coils independently sensing respective components of said central eddy currents and said peripheral eddy currents.

3. The eddy current probe of claim 2 wherein:
said flow of alternating current through said outer drive coil is activated independently of said flow of alternating current through said central core drive coil.

4. The eddy current probe of claim 2 wherein:
said plurality of interstices and plurality of partitions together form a castellated structure composed of essentially prismatic partitions separated by essentially straight sided crenelated openings.

5. An eddy current probe comprising:
a body formed of a high permeability material, said body including a central core, a radially extending wall radiating from said central core, and a circumferentially extending wall extending from said radially extending wall concentrically with said central core, said circumferentially extending wall including a rim distal from said radial wall, said rim including a plurality of interstices dividing said rim into a plurality of partitions that are symmetrically located about said rim, each of said partitions being shaped so as to include a portion thereof that extends in a plane that is essentially perpendicular to an axis of said central core;
a central core drive coil wound around a surface of said central core facing said circumferentially extending wall, said central core drive coil generating a first magnetic field for inducing central eddy currents in a workpiece upon activation of a flow of alternating current through said central core drive coil;
a plurality of independent sense coils equal in number to the number of said partitions with a respective one of said independent sense coils being wound around that portion of a respective one of said partitions that extends in said plane such that each of said partitions includes an associated independent sense coil wound around it,
each of said independent sense coils independently sensing a respective component of said central eddy currents; and,
an outer drive coil wound around an outer surface of said circumferentially extending wall away from said central core, said outer drive coil generating a second magnetic field for inducing peripheral eddy currents in said workpiece upon activation of a flow of alternating current through said outer drive coil,
said flow of alternating current through said outer drive coil being activated independently of said flow of alternating current through said central core drive coil,
each of said independent sense coils independently sensing a respective component of said peripheral eddy currents.

6. An eddy current probe comprising:
a first body formed of a high permeability material, said first body including a central core, a radially extending wall radiating from said central core, and a circumferentially extending wall extending from said radially extending wall concentrically with said central core, said circumferentially extending wall including a solid lip distal from said radially extending wall;
a central core drive coil wound around a surface of said central core facing said circumferentially extending wall, said central core drive coil generating a first magnetic field for inducing central eddy currents in a workpiece upon activation of a flow of alternating current through said central core drive coil;
a second body mounted to said lip, said second body comprising a plurality of individual sections symmetrically arrayed with respect to said central core; and,
a plurality of transducers, equal in number to the number of said sections of said second body, located on said second body, a respective one of said transducers being positioned in a respective one of said sections operatively associated with it, said transducers being positioned in at least one symmetrical array with respect to said central core,
each of said transducers independently sensing a respective component of said central eddy currents.

7. The eddy current probe of claim 6 wherein said each of said transducers comprises a sense coil embedded in said associated section.

8. The eddy current probe of claim 7 wherein at least a portion of said second body is formed of a high permeability material.

9. The eddy current probe of claim 8 wherein said portion of said second body comprises a plurality of sense coil cores formed of said high permeability material, each said sense coil core being embedded in said second body within a respective one of said sense coils.

10. The eddy current probe of claim 7, further comprising a plurality of ferrite rods, equal in number to the number of said sense coils, embedded in said second body, a respective one of said sense coils being wound around a respective one of said ferrite rods.

11. The eddy current probe of claim 7 wherein each of said sense coils is embedded in said second body such that said each of said sense coils is positioned in essentially parallel alignment with said central core of said first body.

12. The eddy current probe of claim 7 wherein each of said sense coils is embedded in said second body such that said each of said sense coils is positioned in a plane essentially perpendicular to an axis of said central core of said first body.

13. The eddy current probe of claim 6, further comprising an outer drive coil wound around an outer surface of said circumferentially extending wall away from said central core, said outer drive coil generating a second magnetic field for inducing peripheral eddy currents in said workpiece upon activation of a flow of alternating current through said outer drive coil,
said flow of alternating current through said outer drive coil being activated independently of said flow of alternating current through said central core drive coil,
each of said transducers independently sensing a respective component of said peripheral eddy currents.

14. The eddy current probe of claim 11, further comprising an outer drive coil wound around an outer surface of said circumferentially extending wall away from said central core, said outer drive coil generating a second magnetic field for inducing peripheral eddy currents in said workpiece upon activation of a flow of alternating current through said outer drive coil, said flow of alternating current through said outer drive coil being activated independently of said flow of alternating current through said central core drive coil, each of said sense coils independently sensing a respective component of said peripheral eddy currents.

15. The eddy current probe of claim 12, further comprising an outer drive coil wound around an outer surface of said circumferentially extending wall away from said central core, said outer drive coil generating a second magnetic field for inducing peripheral eddy currents in said workpiece upon activation of a flow of alternating current through said outer drive coil, said flow of alternating current through said outer drive coil being activated independently of said flow of alternating current through said central core drive coil, each of said sense coils independently sensing a respective component of said peripheral eddy currents.

16. The eddy current probe of claim 6, wherein:

said plurality of transducers are positioned in said second body in a first circular symmetrical array and a second circular symmetrical array, said transducers of said first circular symmetrical array being positioned in alternating sequence with said transducers of said second circular symmetrical array at equal arcuate distances with respect to said central core, said first circular symmetrical array being positioned at a first radial distance with respect to said central core, said second circular symmetrical array being positioned at a second radial distance from said central core, said second radial distance being different from said first radial distance.

17. The eddy current probe of claim 6, further comprising:

a central bore extending within said central core;

a central body adapted for retention in said central bore and having a central boss extending within said central bore concentric with and spaced from a surface of said central bore;

a central body coil wound around said central boss, said central body coil generating centering eddy currents in said workpiece upon activation of a flow of alternating current through said central body coil.

18. The eddy current probe of claim 6 wherein each of said transducers comprises a Hall effect sensor element.

19. The eddy current probe of claim 6 further comprising means engaging said circumferentially extending wall of said first body for guiding a motion of said first body in a closed orbit about a point that is off-center from the center of said central core.

20. The eddy current probe of claim 6, further comprising:

an axle mounted to said radially extending wall and extending away from said central core at a radial offset distance from an axis of said central core; and, means connected to said axle for rotating said probe about said axle.

21. The eddy current probe of claim 6, further comprising:

a case mounted to said second body along a perimeter of said second body, said first body being enclosed within said case and said second body;

an axle mounted to said radially extending wall and extending away from said central core through a clearance bore in said case at a radial offset distance from an axis of said central core; and, means connected to said axle for rotating said first body about said axle.

22. An eddy current probe comprising:

a body formed of a high permeability material, said body being shaped to include a central core, a radially extending wall radiating from said central core, and a circumferentially extending wall extending from said radially extending wall concentrically with said central core, said central core having a central axis;

a central core drive coil wound around a surface of said central core facing said circumferentially extending wall, said central core drive coil generating a first magnetic field for inducing central eddy currents in a workpiece upon activation of a flow of alternating current through said central core drive coil;

a plurality of transducer means for sensing eddy currents, each of said transducer means being positioned in operative association with said circumferentially extending wall in a symmetrical circular array, each of said transducer means independently sensing a respective component of said central eddy currents;

means engaging said body for moving said body in a prescribed closed orbit; and, an outer drive coil wound around an outer surface of said circumferentially extending wall away from said central core, said outer drive coil generating a second magnetic field for inducing peripheral eddy currents in said workpiece upon activation of a flow of alternating current through said outer drive coil, said flow of alternating current through said outer drive coil being activated independently of said flow of alternating current through said central core drive coil, said each of said transducer means independently sensing a respective component of said peripheral eddy currents.

23. The eddy current probe of claim 22 wherein said means for moving said body in a prescribed closed orbit moves said body in an orbit about an off-center axis, said off-center axis being parallel to and radially displaced from said central axis of said central core.

24. The eddy current probe of claim 23 wherein:

said body includes an axle extending from said radially extending wall away from said central core in axial alignment with said off-center axis; and, said means for moving said body in a prescribed closed orbit engages said axle and rotates said body about said axle.

25. The eddy current probe of claim 23 wherein:

said means for moving said body in a prescribed closed orbit comprises a guide, said guide having a circular central aperture wall engaging said body; and, said means for moving said body in a prescribed closed orbit moves said body in said prescribed closed orbit about said off-center axis in contact with said central aperture wall without rotation of said body about said off-center axis.

26. An eddy current probe comprising:
   a first body formed of a high permeability material, said first body including a central core, a radially extending wall radiating from said central core, and a circumferentially extending wall extending from the radially extending wall concentrically with said central core, said circumferentially extending wall having a rim distal from said radially extending wall;
   a central core drive coil wound around a surface of said central core facing said circumferentially extending wall, said central core drive coil generating a first magnetic field for inducing central eddy currents in a workpiece upon activation of a flow of alternating current through said central core drive coil;
   a second body movably engaging said rim, said second body being symmetrically divided into a plurality of individual sections;
   a plurality of transducer means, equal in number to the number of said sections of said second body, for sensing eddy currents, said transducer means being positioned on said second body with a respective one of said transducer means positioned in a respective one of said sections operatively associated with it, said plurality of transducer means being positioned in at least one symmetrical array with respect to said rim of said circumferentially extending wall, each of said transducer means independently sensing a respective component of said central eddy currents;
   a case mounted to said second body along a perimeter of said second body, said case enclosing said first body; and
   means for moving said first body in a prescribed closed orbit with respect to said second body within said case.

27. The eddy current probe of claim 26 wherein:
   said second body includes a central axis, said central axis being located parallel to and radially displaced from an axis of said central core of said first body;
   said first body includes an axle extending from said radially extending wall away from said central core through a clearance bore in said case in axial alignment with said central axis; and,
   said means for moving said first body in a prescribed closed orbit with respect to said second body engages said axle and moves said first body in an orbit centered on said central axis of said second body.

28. The eddy current probe of claim 27 wherein said means for moving said first body in a prescribed closed orbit rotates said first body about said central axis of said second body.

29. The eddy current probe of claim 27 wherein said central axis is an axis of symmetry of said symmetrical array, said means for moving said first body moving said central core and said central core drive coil in oscillating movement with respect to said case without rotation of said first body about said central axis of said second body.

30. An eddy current probe comprising:
   a first body formed of a high permeability material, said first body being shaped to include a central core, a radial wall radially extending from said central core, and a circumferentially extending wall extending from the radial wall concentrically with said central core, said circumferentially extending wall including a lip distal from said radial wall;
   a central core drive coil wound around a surface of said central core facing said circumferentially extending wall, said central core drive coil generating a first magnetic field for inducing central eddy currents in a workpiece upon activation of a flow of alternating current through said central core drive coil;
   a second body mounted on said lip of said circumferentially extending wall; and,
   a plurality of Hall effect sensor elements positioned in said second body in at least one symmetrical array relative to said central core, each of said Hall effect sensor elements independently sensing a respective component of said central eddy currents.

31. The eddy current probe of claim 30 wherein said second body is a monolithic body having said Hall effect sensor elements integrally formed thereon.

32. An eddy current probe comprising:
   a first body formed of a high permeability material, said first body being shaped to include a hollow central core, a radially extending wall radiating from said hollow central core, and a circumferentially extending wall extending from said radially extending wall concentrically with said hollow central core, said circumferentially extending wall including a rim distal from said radially extending wall, said rim including a plurality of interstices that divide said rim into a plurality of partitions that are symmetrically located about said circumferentially extending wall, said partitions being shaped so as to extend in essentially parallel alignment with said hollow central core;
   a central core drive coil wound around a surface of said hollow central core facing said circumferentially extending wall, said central core drive coil generating a first magnetic field for inducing central eddy currents in a workpiece upon activation of a flow of alternating current through said central core drive coil;
   a plurality of sense coils, equal in number to the number of said partitions, a respective one of said sense coils being wound around a respective one of said partitions; and
   a centering coil located in a central bore in said hollow central core of said first body, said centering coil generating a centering magnetic field for inducing centering eddy currents in said workpiece upon activation of a flow of alternating current through said centering coil,
   said flow of alternating current through said centering coil being activated independently of said flow of alternating current through said central core drive coil,
   each of said sense coils independently sensing respective components of said central eddy currents and said centering eddy currents.

33. The eddy current probe of claim 32 further comprising:
   a central core body adapted for retention in said central bore of said hollow central core,
   said central core body having a central boss formed of a high permeability material extending within said central bore concentric with and spaced from a surface of said central bore, said centering coil being wound around said central boss.

34. The eddy current probe of claim 32 further comprising:
- an outer drive coil wound around an outer surface of said circumferentially extending wall away from said hollow central core, said outer drive coil generating a second magnetic field for inducing peripheral eddy currents in said workpiece upon activation of a flow of alternating current through said outer drive coil,
- said flow of alternating current through said outer drive coil being activated independently of said flow of alternating current through said central core drive coil and said flow of alternating current through said centering coil,
- said each of said sense coils independently sensing a respective component of said peripheral eddy currents.

35. An eddy current probe comprising:
- a linear body formed of a high permeability material, said linear body having a first solid elongated section, a first plurality of individual partitions and a second plurality of individual partitions,
- said first solid elongated section having opposing first and second sides that extend along the elongated dimension of said first solid elongated section,
- said first plurality of individual partitions being located in a first linear array along said first side of said first solid elongated section,
- said second plurality of individual partitions being located in a second linear array along said second side of said first solid elongated section,
- said individual partitions of said first linear array each being spaced apart from one another and each orientated essentially perpendicular to said first solid elongated section and essentially mutually parallel to each other,
- said individual partitions of said second linear array each being spaced apart from one another and each orientated essentially perpendicular to said first solid elongated section and essentially mutually parallel to each other;
- a first drive coil wound around said first solid elongated section in the elongated dimension of said first solid elongated section between said first and second sides of said first solid elongated section, said first drive coil generating a first magnetic field for inducing first eddy currents in a workpiece upon activation of a flow of alternating current through said first drive coil; and
- a plurality of individual sense coils, equal in number to the number of said second partitions, a respective one of said sense coils being wound around a respective one of said partitions of said second plurality of partitions, each of said sense coils independently sensing a respective component of said first eddy currents.

36. The eddy current probe of claim 35 further comprising an outer drive coil wound around a periphery of said first solid elongated section encompassing said first and second sides of said first elongated section,
- said outer drive coil generating a peripheral magnetic field for inducing peripheral eddy currents in said workpiece upon activation of a flow of alternating current through said outer drive coil,
- said flow of alternating current through said outer drive coil being activated independently of said flow of alternating current through said first drive coil,
- each of said sense coils independently sensing a respective component of said peripheral eddy currents.

37. The eddy current probe of claim 35 further comprising:
- a second solid elongated section and a third plurality of individual partitions,
- said second solid elongated section having opposing mating and distal sides that extend along the elongated dimension of said second solid elongated section,
- said mating side of said second solid elongated section being joined to said first solid elongated section along said second side of said first solid elongated section such that said first and second solid elongated sections are co-planar and parallel with each other and said second linear array is positioned at said joining of said first and said second solid elongated sections,
- said third plurality of individual partitions being located in a third linear array along said distal side of said second solid elongated section,
- said individual partitions of said third linear array each being spaced apart from one another and each orientated essentially perpendicular to said second solid elongated section and essentially mutually parallel to each other;
- a second drive coil wound around said second solid elongated section in the elongated dimension of said second solid elongated section between said mating and distal sides of said second solid elongated section, said second drive coil generating a second magnetic field for inducing second eddy currents in said workpiece upon a flow of alternating current through said second drive coil; and,
- an outer drive coil wound around a periphery of said joined first and second solid elongated sections encompassing said first side of said first solid elongated section and said distal side of said second solid elongated section,
- said outer drive coil generating a peripheral magnetic field for inducing peripheral eddy currents in said workpiece upon activation of a flow of alternating current through said outer drive coil,
- said flow of alternating current through said outer drive coil being activated independently of said flows of alternating current through said first and second drive coils,
- each of said sense coils independently sensing a respective component of said peripheral eddy currents.

38. The eddy current probe of claim 22, further comprising:
- a central bore extending within said central core;
- a central body adapted for retention in said central bore and having a central boss extending within said central bore concentric with and spaced from a surface of said central bore;
- a central body coil wound around said central boss, said central body coil generating centering eddy currents in said workpiece upon activation of a flow of alternating current through said central body coil.

39. The eddy current probe of claim 26, further comprising an outer drive coil wound around an outer surface of said circumferentially extending wall away from said central core, said outer drive coil generating a second magnetic field for inducing peripheral eddy currents in said workpiece upon activation of a flow of alternating current through said outer drive coil, said flow of alternating current through said outer drive coil being activated independently of said flow of alternating current through said central core drive coil, said each of said transducer means independently sensing a respective component of said peripheral eddy currents.

40. The eddy current probe of claim 26, further comprising:
a central bore extending within said central core;
a central body adapted for retention in said central bore and having a central boss extending within said central bore concentric with and spaced from a surface of said central bore;
a central body coil wound around said central boss, said central body coil generating centering eddy currents in said workpiece upon activation of a flow of alternating current through said central body coil.

41. The eddy current probe of claim 30, further comprising an outer drive coil wound around an outer surface of said circumferentially extending wall away from said central core, said outer drive coil generating a second magnetic field for inducing peripheral eddy currents in said workpiece upon activation of a flow of alternating current through said outer drive coil, said flow of alternating current through said outer drive coil being activated independently of said flow of alternating current through said central core drive coil, said each of said Hall effect sensor elements independently sensing a respective component of said peripheral eddy currents.

42. The eddy current probe of claim 30, further comprising:
a central bore extending within said central core;
a central body adapted for retention in said central bore and having a central boss extending within said central bore concentric with and spaced from a surface of said central bore;
a central body coil wound around said central boss, said central body coil generating centering eddy currents in said workpiece upon activation of a flow of alternating current through said central body coil.

* * * * *